(12) United States Patent
Hancock et al.

(10) Patent No.: US 10,342,595 B2
(45) Date of Patent: Jul. 9, 2019

(54) DUAL-FUNCTION PLASMA AND NON-IONISING MICROWAVE COAGULATING ELECTROSURGICAL INSTRUMENT AND ELECTROSURGICAL APPARATUS INCORPORATING THE SAME

(71) Applicant: CREO MEDICAL LIMITED, Chepstow, Monmouthshire (GB)

(72) Inventors: Christopher Paul Hancock, Bath (GB); Malcolm White, Monmouthshire (GB); Philip William Hales, Wales (GB); Brian Saunders, Rickmansworth (GB); Sandra May Bernadette Holmes, Stevenage (GB)

(73) Assignee: CREO MEDICAL LIMITED, Chepstow, Monmouthshire (GB)

( * ) Notice: Subject to any disclaimer, the term of this patent is extended or adjusted under 35 U.S.C. 154(b) by 797 days.

(21) Appl. No.: 14/890,426

(22) PCT Filed: May 13, 2014

(86) PCT No.: PCT/GB2014/051468
§ 371 (c)(1),
(2) Date: Nov. 10, 2015

(87) PCT Pub. No.: WO2014/184544
PCT Pub. Date: Nov. 20, 2014

(65) Prior Publication Data
US 2016/0113700 A1    Apr. 28, 2016

(30) Foreign Application Priority Data

May 13, 2013 (GB) .................................. 1308558.4

(51) Int. Cl.
*A61B 18/18* (2006.01)
*A61B 18/04* (2006.01)
(Continued)

(52) U.S. Cl.
CPC .......... *A61B 18/042* (2013.01); *A61B 18/148* (2013.01); *A61B 18/1815* (2013.01);
(Continued)

(58) Field of Classification Search
CPC ... A61B 18/18; A61B 18/1815; A61B 18/042; A61B 2018/1823; A61B 2018/1838;
(Continued)

(56) References Cited

U.S. PATENT DOCUMENTS 5,306,238 A * 4/1994 Fleenor ................ A61B 18/042
606/42
6,063,084 A * 5/2000 Farin .................. A61B 18/1492
606/40
(Continued)

FOREIGN PATENT DOCUMENTS

CN      101505674 A    8/2009
GB      2 486 343 A    6/2012
(Continued)

OTHER PUBLICATIONS

English Translation of Chinese Search Report of related Chinese Patent Application No. 2014800395381 dated Jan. 9, 2017.
(Continued)

*Primary Examiner* — Thomas A Giuliani
(74) *Attorney, Agent, or Firm* — Arent Fox LLP

(57) ABSTRACT

An electrosurgical device that is capable of both generating a plasma to perform surface coagulation and emitting a non-ionizing microwave field (in the absence of plasma) to perform coagulation at a deeper level. The device comprises a probe tip that is connected to receive radiofrequency (RF) and/or microwave frequency energy from a generator, and also defines a flow path for a gas. The probe tip is adjustable between a first configuration, in which it defines a bipolar (e.g. coaxial) structure to produce a high electric field from
(Continued)

the received RF and/or microwave frequency energy across the flow path for the gas to strike and sustain plasma and a second configuration, in which it defines an antenna structure to emit non-ionizing microwave energy into tissue.

23 Claims, 15 Drawing Sheets

(51) Int. Cl.
  *A61N 1/40* (2006.01)
  *A61N 1/44* (2006.01)
  *A61N 1/06* (2006.01)
  *A61B 18/14* (2006.01)
  *A61B 18/00* (2006.01)

(52) U.S. Cl.
  CPC ............... *A61N 1/06* (2013.01); *A61N 1/40* (2013.01); *A61N 1/44* (2013.01); *A61B 2018/005* (2013.01); *A61B 2018/00327* (2013.01); *A61B 2018/00404* (2013.01); *A61B 2018/00494* (2013.01); *A61B 2018/00559* (2013.01); *A61B 2018/00577* (2013.01); *A61B 2018/00589* (2013.01); *A61B 2018/00642* (2013.01); *A61B 2018/00666* (2013.01); *A61B 2018/00702* (2013.01); *A61B 2018/00744* (2013.01); *A61B 2018/00785* (2013.01); *A61B 2018/00863* (2013.01); *A61B 2018/00869* (2013.01); *A61B 2018/00875* (2013.01); *A61B 2018/1853* (2013.01); *A61B 2018/1861* (2013.01)

(58) Field of Classification Search
  CPC .... A61B 2018/1853; A61B 2018/1876; A61B 2018/1884; A61B 2018/1861; A61B 2018/00589; A61B 2018/00642; A61B 2018/00785; A61B 2018/122; A61N 1/40; A61N 1/06; A61N 1/44

USPC .................................. 606/33, 40, 41, 42, 49
See application file for complete search history.

(56) References Cited

U.S. PATENT DOCUMENTS

| | | | |
|---|---|---|---|
| 6,391,027 B1* | 5/2002 | Farin | A61B 18/042 606/34 |
| 7,758,537 B1 | 7/2010 | Brunell et al. | |
| 9,333,034 B2* | 5/2016 | Hancock | A61B 18/042 |
| 9,636,176 B2* | 5/2017 | Hancock | A61B 18/1815 |
| 2003/0028189 A1 | 2/2003 | Woloszko et al. | |
| 2005/0149012 A1 | 7/2005 | Penny et al. | |
| 2010/0145328 A1 | 6/2010 | Hancock et al. | |
| 2013/0267943 A1* | 10/2013 | Hancock | A61B 18/042 606/33 |
| 2013/0289557 A1* | 10/2013 | Hancock | A61B 18/1815 606/33 |
| 2017/0014184 A1* | 1/2017 | Hancock | A61B 18/042 |

FOREIGN PATENT DOCUMENTS

| | | |
|---|---|---|
| GB | 2 487 199 A | 7/2012 |
| GB | 2 487 288 A | 7/2012 |
| WO | WO 93/05721 A1 | 4/1993 |
| WO | WO 2007/099460 A2 | 9/2007 |
| WO | WO 2009/060213 A1 | 5/2009 |
| WO | WO 2012/076844 A1 | 6/2012 |
| WO | WO 2012/095653 A1 | 7/2012 |

OTHER PUBLICATIONS

Japanese Office Action of related Japanese Patent Application No. 2016-513434 dated Feb. 20, 2018.
International Search Report and Written Opinion of PCT/GB2014/051468 dated Jul. 23, 2014.

* cited by examiner

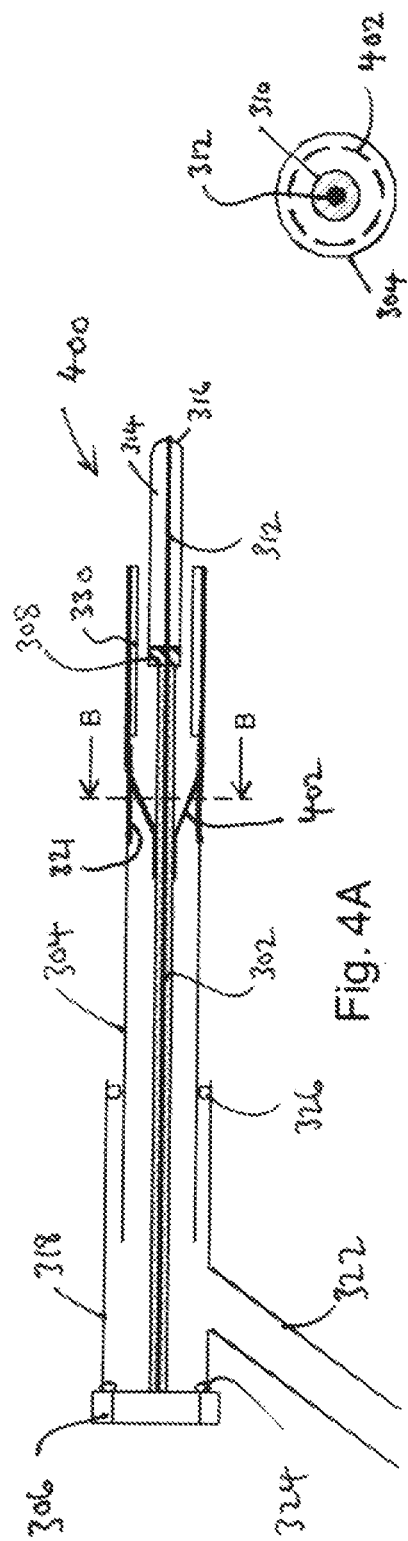
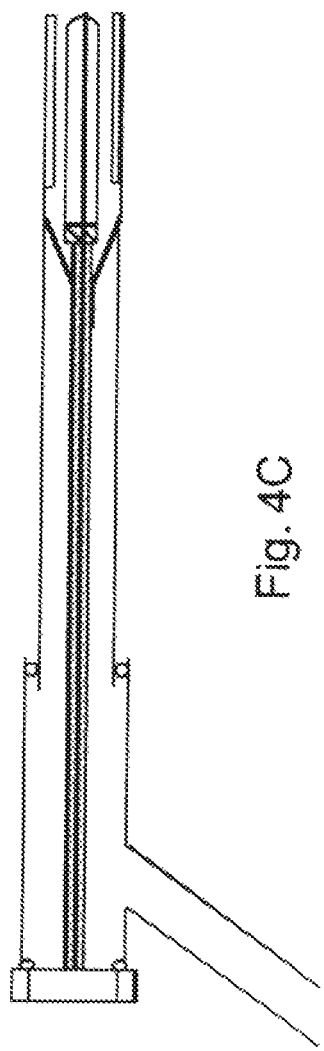
Fig. 4A
Fig. 4B
Fig. 4C

DUAL-FUNCTION PLASMA AND NON-IONISING MICROWAVE COAGULATING ELECTROSURGICAL INSTRUMENT AND ELECTROSURGICAL APPARATUS INCORPORATING THE SAME

CROSS-REFERENCE TO RELATED APPLICATION

This application is a National Stage entry of International Application No. PCT/GB2014/051468, filed May 13, 2014, which claims priority to United Kingdom Patent Application No. 1308558.4, filed May 13, 2013. The disclosures of the priority applications are incorporated in their entirety herein by reference.

FIELD OF THE INVENTION

The invention relates to electrosurgical apparatus in which radiofrequency and/or microwave frequency energy is used to treat biological tissue by causing haemostasis (i.e. sealing broken blood vessels by promoting blood coagulation). In particular, the invention relates to surgical apparatus in which the radiofrequency (RF) and/or microwave energy is used in conjunction with a flow of gas to strike and sustain a thermal plasma.

BACKGROUND TO THE INVENTION

Argon plasma coagulation (APC) or argon beam coagulation (ABC) is a known surgical technique for controlling surface bleeding in a manner that does not require physical contact between a surgical probe delivering the plasma and the lesion. APC can be performed endoscopically, whereby a jet of argon gas is directed through a probe passed through an endoscope. Ionization of the argon gas as it is emitted creates the plasma that causes coagulation.

To strike plasma it is desirable to have a high electric field (e.g. high voltage or high impedance condition). Accordingly, it is necessary to set-up a high impedance state in order to enable the high voltage (high electric field) necessary to break down the gas to generate plasma. In one embodiment discussed in WO 2009/060213, a high voltage (high impedance) condition is set up using a flyback circuit that uses a low frequency (e.g. radiofrequency) oscillator circuit and a transformer whose primary winding is connected to the low frequency oscillator circuit by a suitable driver and switching device (e.g. gate drive chip and a power MOSFET or BJT). The arrangement generates high voltage pulses or spikes which strike or otherwise initiate the plasma. Once struck, the plasma may be maintained by a supply of microwave energy.

SUMMARY OF THE INVENTION

At its most general, the present invention provides an electrosurgical device that is capable of both generating a plasma to perform surface coagulation and emitting a non-ionising microwave field (in the absence of plasma) to perform coagulation at a deeper level. The former functionality may be useful in the same way as the conventional APC technique, e.g. for treating surface bleeding. The latter functionality may be used to treat peptic ulcers or coagulate large blood vessels.

To achieve the dual functionality expressed above, the electrosurgical device of the invention comprises a probe tip that is adjustable between two configurations. The probe tip is connected to receive radiofrequency (RF) and/or microwave frequency energy from a generator, and also defines a flow path for a gas. In a first configuration, the probe tip defines a bipolar (e.g. coaxial) structure to produce a high electric field from the received RF and/or microwave frequency energy across the flow path for the gas to strike and sustain plasma. In a second configuration, the probe tip defines an antenna structure to emit non-ionising microwave energy into tissue. The antenna structure may be a radiating monopole antenna, which may take the form of a cylinder, a ball, a stiff wire or a helix or a turnstile antenna that is capable of emitting outwardly (i.e. away from the probe) an electric field from the received microwave frequency energy. Thus, in the first configuration the device may use one or both of RF energy and microwave energy, whereas in the second configuration, the device preferably uses microwave energy.

The bipolar structure may comprise inner and outer conductors. The outer conductor may be retractable relative to the inner conductor to adjust the probe tip between the first configuration and second configuration. For example, where the inner conductor and outer conductor are arranged coaxially, the outer conductor may retract from a first position (corresponding to the first configuration) where it surrounds the inner conductor, to a second position (corresponding to the second configuration) where it is axially displaced rearwards (i.e. towards the proximal end of the device) to expose the inner conductor.

In the first configuration, the plasma may be struck using RF or microwave energy. Microwave energy may be used to sustain the plasma after it is struck. This arrangement may offer an advantage over RF plasma used in conventional electrosurgical systems, where the electric field may collapse due to the capacitance of the cable and loading caused by tissue variations.

The impedance of the plasma is preferably matched to the impedance of the applicator (and energy delivery system) at the frequency of the microwave energy to enable efficient transfer of the microwave energy, produced by the microwave source, into the plasma. Where microwave energy is used, the applicator and/or generator may be tuned (statically or dynamically) to ensure that the plasma is matched into the load presented by the tissue. At microwave frequencies, the cable forms a distributed element transmission line, where the impedance match between applicator and energy source is determined by the source impedance of the microwave generator, the characteristic impedance of the cable (transmission line), the impedance of the applicator structure itself and the impedance of the tissue. If the characteristic impedance of the cable is the same as the output impedance of the source then all of the microwave power will be delivered into the applicator, less the attenuation caused by the cable (dielectric and conductor losses). If the impedance of the applicator and the tissue is the same as the characteristic impedance of the cable, then the maximum power available at the source will be transferred into the plasma/tissue load. Adjustments may be made to applicator structure in order to maintain the best impedance match between the applicator and the plasma/tissue load, as explained below. Adjustments may also be made at the generator or at the interface between the distal end of the first cable and the proximal end of the second (instrument) cable. These adjustments may be in the form of a change of capacitance and/or inductance of a matching network, i.e. stub tuning.

In this specification "microwave frequency" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz.

According to one aspect of the invention, there is provided an electrosurgical instrument comprising: an elongate probe comprising a coaxial cable for conveying radiofrequency (RF) and/or microwave frequency electromagnetic (EM) energy, and a probe tip connected at the distal end of the coaxial cable for receiving the RF and/or microwave energy; and a gas passage for conveying gas through the elongate probe to the probe tip, wherein the coaxial cable comprises an inner conductor, an outer conductor and a dielectric material separating the inner conductor from the outer conductor, wherein the probe tip comprising a first electrode connected to the inner conductor of the coaxial cable and a second electrode connected to the outer conductor of the coaxial cable, and wherein the first electrode and second electrode are movable relative to each other between: a first configuration in which they are arranged to produce an electric field from the received RF and/or microwave frequency EM energy across a flow path of gas received from the gas passage to produce a thermal or non-thermal plasma, and a second configuration in which the first electrode extends distally beyond the second electrode to form a radiating structure for emitting a microwave EM field outwardly from the probe tip. Thus, in the first configuration the instrument may operate to produce a plasma suitable for surface (or superficial) coagulation of biological tissue and/or sterilisation/disinfection of biological tissue or instruments. The gas may be argon, or any other suitable gas, e.g. carbon dioxide, helium, nitrogen, a mixture of air and any one of these gases, i.e. 10% air/90% helium. The high electric field for striking the plasma may be caused by creating a high impedance condition for either the RF EM energy or the microwave EM energy at the probe tip. This can be achieved through the selection of a suitable geometry for the first and second electrodes. For example, a piece of insulating dielectric material, such as quartz or other similarly low loss material, may be located between the first and second electrodes in the first configuration. This may increase the impedance and therefore facilitate the creation of a high electric field. In the first configuration, the second electrode may be arranged to extend past (e.g. more distally than) the first conductor to ensure that non-ionising radiation is not emitted.

In the second configuration, the probe can radiate microwave frequency energy in the form of a microwave EM field for deeper coagulation of biological tissue or sterilisation.

In a preferred embodiment, the instrument is capable of receiving both RF and microwave EM energy. The RF EM energy may be for striking the plasma, and may be received as a high voltage pulse. The microwave EM energy is for sustaining the plasma, i.e. delivering power into the plasma to maintain the state of ionisation. This may also be received as a pulse. The plasma may be struck repeatedly in a manner to produce a quasi-continuous beam of plasma. The advantage of this arrangement over conventional APC device which use only RF EM energy is that the plasma will not collapse due to capacitive loading or changing from a dry to wet environment. Moreover, the dual configuration nature of the instrument enables it to switch to a state suitable for deep coagulation, where the second electrode (and the insulating dielectric material) are withdrawn to a distance where the first electrode is exposed such that is acts as a radiating microwave monopole antenna structure as discussed below.

It may also be possible to strike the plasma using the microwave frequency energy, e.g. by using a microwave resonator or an impedance transformer, i.e. a quarter wave transformer that transforms a low voltage to a higher voltage to strike plasma using a higher impedance transmission line that is a quarter wave (or an odd multiple thereof) long at the frequency of operation. This high impedance line may be switched in to strike plasma and switched out (i.e. to return to a lower impedance line) once the plasma has been struck and it is required to sustain plasma. A power PIN or varactor diode may be preferably used to switch between the two states, although it may be possible to use a co-axial or waveguide switch.

The elongate probe may comprise a sleeve surrounding the coaxial cable. The sleeve may act to protect the coaxial cable, but may also define the gas passage, e.g. as a space between an inside surface of the sleeve and an outside surface of the coaxial cable. The gas passage may have an input port located at a proximal end of the sleeve for connecting to a source of gas (e.g. a pressurised gas canister or the like).

The sleeve may further be the means for causing relative movement between the first and second electrodes. Relative movement between the first and second electrodes may be achieved by sliding a conductive (e.g. metallic) catheter over a microwave co-axial cable, whose outer conductor may also metallic. In this configuration the inner surface of the catheter (or tube that slides over the co-axial cable) must make good electrical contact with the outer conductor of the coaxial cable. This may be achieved by providing a gas permeable conductive structure that is slidable relative to the second electrode or outer electrode of the coaxial cable and permits gas to flow through it. The gas permeable conductive structure may be any one of: a conductive mesh; a cage of radially extending conductive wires or springs; and a plurality of circumferentially spaced radially protruding dents. The gas permeable conductive structure may thus provide a plurality of (e.g. four or more) circumferential connections or point contacts will need to be made to ensure that a good electrical connection is made for the microwave signal. This solution may provide a balance between having enough connection points to create an appropriate environment for the microwave energy to propagate, to allow enough gas to flow and allow the outer catheter to be moved over the co-axial cable with relative ease.

In one embodiment, the second electrode may be mounted on or formed at the distal end of the sleeve, and the sleeve may be retractable relative to the coaxial cable. In other words, the sleeve may be capable of being drawn back to reveal the first electrode at the probe tip. The sleeve may be coaxial with the coaxial cable. The first and second electrodes may thus be coaxial with each other in the first configuration. The second electrode may be an annular band of conductive material on the distal end of the sleeve. The dielectric material mentioned above may be a quartz collar mounted on the sleeve inwardly of the annular band. Alternatively or additionally, the dielectric material may be part of the inner electrode, as discussed below.

The retracting sleeve may comprise two or more telescoping sections. The telescoping sections may have a fluid tight seal therebetween to prevent the gas from escaping. The slidable outer sleeve may be retracted or extended using a mechanical or electromechanical system, i.e. a mechanical slider, a linear motor or a stepper motor arrangement. As explained below, the position of the outer sleeve with respect to the outer conductor of the co-axial cable may be determined by a return loss or impedance match/mismatch measurement made using a reflected power or forward and reflected power measurement, i.e. a reflectometer or VSWR bridge measurement, using a detector(s) within the generator or within the probe.

In an alternative embodiment, the coaxial cable itself may be movable within the sleeve. In this arrangement the sleeve may be secured, e.g. fixed, to a proximal handpiece, which may include a manual slider or any of the movement mechanisms mentioned herein for sliding the coaxial cable within the sleeve.

The first electrode may be a radiating microwave monopole antenna structure coupled to receive RF and/or microwave EM energy from the coaxial cable. The outer conductor of the coaxial cable may be grounded to form an unbalanced feed or may be floating to form a balanced feed to the antenna, i.e. where the voltage on both conductors is going up and down. Preferably the first electrode is shaped to act as a microwave antenna for emitting a microwave field corresponding to the received microwave EM radiation. For example, the monopolar radiating structure may comprise a cylinder of dielectric material having a hemispherical distal end surrounding a length of the inner conductor of the coaxial cable which protrudes beyond the outer conductor and extends through the cylinder of dielectric material to protrude at its hemispherical distal end. Other distal end shapes are possible, e.g. ball or flat end. The cylinder may be made of low loss ceramic material. The presence of the dielectric cylinder can improve the energy delivery into tissue, e.g. by reducing the amount of reflected power. The end of the length of inner conductor that protrudes from the hemispherical distal end of the cylinder may be rounded, e.g. shaped into a hemisphere, to provide a more uniform emitted field.

Preferably the monopolar radiating structure (i.e. the first electrode in the second configuration) is arranged to be well matched to the impedance of blood at the frequency of the microwave EM radiation to produce non-ionising radiation that is efficiently coupled into blood to cause controlled coagulation.

The outer electrode of the coaxial cable may be connected to the second electrode by a conductive mesh that permits gas to flow through it. The conductive mesh may therefore be mounted in the passage in the probe, i.e. in the space between the coaxial cable and the sleeve. Alternatively, the space between the coaxial cable and the sleeve may be divided into a plurality of sub-passages, e.g. by divider elements connected to or part of the sleeve. In this situation, the divider elements or a separate connector element may provide an electrical connection between the outer conductor of the coaxial cable and the second electrode. The connection may also be made by one flexible wire or strip, which may be soldered or crimped to the second electrode.

The probe may be used laparoscopically or may be dimensioned to be insertable through a scoping device, e.g. through the instrument channel of an endoscope, gastroscope, bronchoscope or the like. For example, the coaxial cable may have a diameter of 2.5 mm or less, preferably 2.2 mm or less. The sleeve may have an outer diameter less than 2.6 mm, preferably less than 2.5 mm. For larger laparoscopic instruments, the outer diameter may be 3 mm or more, and larger diameter co-axial cable may be used.

According to another aspect of the invention, there is provided electrosurgical apparatus for performing coagulation comprising: a microwave signal generator for generating microwave EM energy; an electrosurgical instrument as described above connected to receive the microwave EM energy; a feed structure for conveying the microwave EM energy to the probe, the feed structure comprising a microwave channel for connecting the probe to the microwave signal generator, a gas feed connected to supply gas to electrosurgical instrument, wherein the apparatus is operable: in a surface coagulation mode when the electrosurgical instrument is in the first configuration and gas is supplied thereto, whereby the microwave EM energy delivered to the probe tip is arranged to strike and/or sustain a gas plasma between the first and second electrodes; and in a deep tissue coagulation mode when the electrosurgical instrument is in the second configuration without gas supplied to thereto, whereby the microwave EM energy delivered to the probe tip is arranged to emit a non-ionising electric field outwardly from the probe tip. The apparatus may include a radiofrequency (RF) signal generator for generating RF electromagnetic (EM) energy having a first frequency, wherein: the microwave frequency EM energy has a second frequency that is higher than the first frequency, the feed structure includes an RF channel for connecting the probe to the RF signal generator, and in the surface coagulation mode, the apparatus is arranged to deliver the RF EM energy to the probe tip to strike the gas plasma between the first and second electrodes.

The apparatus may comprise a strike signal generation circuit arranged to cause a pulse (or pulses) of RF EM radiation to be delivered to the probe to generate the high electric field across the flow path for striking the plasma, wherein the strike signal generation circuit includes control circuitry arranged to use a detectable characteristic of a pulse of microwave EM radiation on the microwave channel to trigger generation of the pulse of RF EM radiation. The RF EM radiation is thus used to strike the plasma, whereas the microwave EM radiation is used to sustain the plasma. By coordinating the delivery of an RF strike pulse with a pulse of microwave EM radiation as described above, the apparatus is capable of striking the plasma with greater certainty.

The apparatus may further comprise a microwave signal detector for sampling forward and reflected power on the microwave channel and generating therefrom a microwave detection signal indicative of the microwave power delivered by the probe; and a controller in communication with the microwave signal detector to receive the microwave detection signal, wherein the controller is operable to select an energy delivery profile for the microwave EM radiation, the energy delivery profile for the microwave EM radiation being for coagulation of tissue, wherein the controller comprises a digital microprocessor programmed to output a microwave control signal for the microwave signal generator, the microwave control signal being for setting the energy delivery profile for the microwave EM radiation, and wherein the controller is arranged to determine a state for the microwave control signal based on the received microwave detection signal. The arrangement may be used to measure the reflected microwave signal, whereby the microwave detection signal is representative of whether or not a plasma has been struck. The signal detector may also be arranged to continuously monitor the forward and reflected microwave EM radiation to ensure that the best impedance match is maintained during plasma delivery. The microwave signal detector may comprise forward and reflected signal detectors (e.g. suitable directional power couplers on the microwave channel). The detectors may be arranged to detect signal magnitude only, e.g. they may be diode detectors. Alternatively, the detectors may be arranged to detect magnitude and phase, e.g. they may be heterodyne detectors. The microwave detection signal may thus be representative of return loss or impedance match information. The relative position of the first and second electrodes of the electrosurgical instrument may be adjustable by the controller in the surface coagulation mode (i.e. when plasma is being generated) until a set return loss threshold is reached, i.e. 8 dB, 10 dB or 12 dB.

The apparatus may include a movement mechanism for causing relative movement between the first electrode and second electrode, wherein the controller is arranged to communicate a control signal to the movement mechanism based on the received microwave detection signal. The movement mechanism may be mechanical, and may be manually controlled, e.g. by the operator of the instrument. The movement mechanism may comprise an actuator, e.g. lever or pull arm, located at the distal end of the instrument, e.g. a sliding or rotating mechanism that is moved by hand.

However, it is also contemplated herein to control the relative movement of the first and second electrode (i.e. setting the first and second configurations) in an automated manner, e.g. using an electromechanical mechanism. For example, in one embodiment, there may be a configuration controller arranged to automatically move the sleeve and operate the gas supply in accordance with the rate of blood flow at the treatment site. This feature may be used to ensure that large bleeds are dealt with in an expedient manner and that the depth of heating of healthy tissue is limited.

Furthermore, the controller may be arranged to automatically operate the movement mechanism as a means for controlling the impedance match into the plasma. Reflected and forward power measurements on the microwave channel may be used to control the position of the outer catheter with respect to the inner co-axial cable (or the inner electrode attached to the co-axial cable) by hand movement or by means of an electromechanical actuator (PZT actuator, a magnetostrictive actuator, stepper motor, linear motor) based on return loss measurements or impedance match. The occurrence of a deep or heavy bleed whilst performing ABC or surface coagulation may cause the plasma to be extinguished, which in turn would lead to the return loss measurement changing, i.e. from 10 dB (good match) to 2 dB (poor match). In the present invention, the outer sleeve may be automatically moved back to allow the microwave antenna to be deployed to enable non-ionising microwave energy to be coupled into the blood or vessel instead of ionising gas (plasma) to produce deeper coagulation to deal with the larger bleeder.

The configuration controller may include a stepper motor or linear motor connected to the sleeve or the coaxial cable to move the first and second electrodes relative to one another. The movement of the first electrode may also be based on a flow rate measurement instead of or as well as the impedance match or return loss measurement. In this instance, the mode of operation is automatically changed from surface coagulation (ABC) to deeper coagulation (extended monopole antenna to deliver non-ionising microwave radiation) to produce deep coagulation based on an increase in the rate of blood flow.

The configuration controller may be connected to a valve to control the gas supply, e.g. to switch off the supply when the instrument moves to the second configuration and to switch it on when the instrument moves to the first configuration. The valve may be part of the instrument, e.g. integrated between the sleeve and the coaxial cable, or it may be located outside the instrument, e.g. in the gas feed.

Moreover, in combination with the microwave signal detector mentioned above, the configuration controller may be arranged to control the position of the sleeve in the first configuration when the plasma is present on the basis of the microwave detection signal to minimise the reflected microwave signal. In other words, the configuration controller comprises a feedback arrangement for fine tuning the position of the sleeve in the first configuration to facilitate efficient delivery of the plasma.

While the instrument may be arranged to generate a thermal plasma when in the first configuration, it may also be arranged to generate a non-thermal plasma for sterilisation. With a co-axial applicator structure that has a plasma generating region with a diameter of between 3 mm and 5 mm, i.e. the inner diameter of the outer conductor within the co-axial structure has a diameter of between 3 mm and 5 mm, and a quartz tube that fits tightly inside with a wall thickness of between 0.25 mm and 1 mm, and where the outer diameter of the inner conductor is between 0.75 mm and 4 mm (allowing a space for gas to flow in the region between the inner conductor and the inner wall of the quartz tube), that a non-thermal plasma suitable for disinfection or sterilisation can be produced by operating the generator in pulsed mode with a duty cycle of less than 40%, i.e. 28%. In one embodiment, the rms power in a single microwave pulse is 50 W and the pulse ON time is 40 ms, within a total period of 140 ms, i.e. the average power delivered into the plasma is 14.28 W at 2.45 GHz. When an RF strike pulse is used in this configuration, the duration of the RF strike pulse is around 1 ms, and the frequency of the sinusoidal oscillations was 100 kHz. The amplitude was around 1 kV peak (707 Vrms). The RF power was less than 10% of the microwave power. The RF pulse was synchronised to the microwave burst or pulse and triggered on the rising edge of the microwave burst or pulse.

To produce thermal plasma, the duty cycle may be increased, i.e. to 50% or continuous wave (CW) and/or the rms power level may be increased, i.e. to 75 W or 100 W for this particular applicator geometry (if the geometry decreased or increased then the microwave power and the amplitude of the RF strike pulse would be adjusted accordingly). The ratio of RF to microwave power will preferably remain constant, i.e. less than 10% for non-thermal and thermal plasma.

Having the ability to perform sterilisation at the distal end of the instrument may be particularly advantageous for the purpose disinfecting the instrument channel of scopes. In order words, the non-thermal plasma is emitting as the instrument is withdrawn from the scope (e.g. endoscope or the like) to treat the inner surface of the instrument. Whilst non-thermal plasma is preferred for this process, it may also be possible to achieve sterilisation by delivering non-ionising microwave RF radiation only, i.e. in the absence of gas.

The sterilising function of the non-thermal plasma may also be used to sterilise body cavities before or after treatment. Where the device is used to clean or sterilise instruments, e.g. endoscopes or gastroscopes, the device may be configured to produce a combination of non-thermal plasma and non-ionising microwave radiation. The device may also be configured to produce non-thermal plasma, thermal plasma and non-ionising microwave radiation where it is used in NOTES procedures or where it is advantageous to be able to perform surface coagulation, sterilisation of body tissue and deep coagulation of large vessels or bleeders.

The apparatus and instrument may thus have four use modes:

non-thermal plasma used to sterilise or disinfect the instrument channel of an endoscope or any other scope or other equipment or to sterilise or disinfect biological tissue or external surfaces non-ionising microwave radiation to sterilise or disinfect the instrument channel of endoscopes, other scopes or other equipment thermal plasma for surface or superficial coagulation non-ionising microwave radiation for deeper coagulation.

In other words, the sleeve of the instrument may be adjustable between four states:

Non-ionising microwave radiation: monopole radiating antenna exposed to emit non-ionising microwave radiation for deep coagulation;

Plasma strike using RF and microwave energy: the radiating monopole is covered by outer sleeve and gas is introduced into the region so that plasma (thermal for surface coagulation and/or non-thermal for sterilisation/disinfection) can be struck and sustained;

Plasma strike using microwave energy only: the proximity between the inner and outer conductors is adjusted to generate a high enough E-field to strike plasma;

Plasma sustain using the microwave field only: the proximity between the inner and outer conductors is adjusted to generate a low impedance environment to allow plasma to be sustained.

The sleeve may have a plurality of predetermined set positions corresponding to each configuration. The instrument may include a mechanism for retaining the sleeve in each one of the set positions, e.g. a locating groove or ratchet mechanism.

The instrument may thus provide four functions: sterilisation using non-thermal plasma, surface tissue coagulation using thermal plasma, deep tissue coagulation using non-ionising microwave radiation and sterilisation using non-ionising microwave radiation. It may be appreciated that having a single instrument capable of performing two or three or four functions as described above enables rapid and efficient treatment because the instrument does not need to be withdrawn if a different function is required.

The RF and microwave EM energy may be delivered separately or simultaneously in any of the use modes of the apparatus. For example, only RF EM energy may be used to strike and sustain the plasma in the surface coagulation mode, and only microwave EM energy may be used only to deliver non-ionising radiation in the deep coagulation mode. Alternatively, a high voltage RF electric field may be created to strike the plasma, followed by a microwave frequency field augmented with a RF field to sustain plasma.

Similarly, the microwave frequency EM energy may be used to augment the RF strike voltage to help guarantee a plasma strike. This may be done by controlling the microwave signal generator to produce peak power for the duration of the RF strike pulse, and then produce a reduced power level to sustain plasma after it has been struck.

In another aspect, the present invention may provide an instrument suited for performing APC where the plasma is struck by a pulse of RF energy and sustained by a pulse of microwave frequency energy. According to this aspect, there may be provided an electrosurgical instrument comprising: an elongate probe comprising a coaxial cable for conveying radiofrequency (RF) and microwave frequency electromagnetic (EM) radiation, and a probe tip connected at the distal end of the coaxial cable for receiving the RF and microwave radiation separately or simultaneously from the coaxial cable; and a gas passage for conveying gas through the elongate probe to the probe tip, wherein the coaxial cable comprises an inner conductor, an outer conductor and a dielectric material separating the inner conductor from the outer conductor, wherein the probe tip comprising a first electrode connected to the inner conductor of the coaxial cable and a second electrode connected to the outer conductor of the coaxial cable, and wherein the first electrode and second electrode are arranged to produce a high electric field from the received RF EM energy across a flow path of gas received from the gas passage in order to strike a plasma, and arranged to deliver the received microwave energy to sustain the plasma after it is struck.

This device may not have the dual functionality discussed above, but instead utilises microwave frequency energy to improve on existing APC systems. The advantage of using combined RF and microwave frequency energy to create the plasma beam is that the energy required to strike the plasma does not rely on an external return path and the energy to sustain the plasma can be accurately controlled to ensure rapid and efficient treatment. Alternatively, the plasma may be generated using the RF only, as is conventional, and the microwave energy may be provided only in order to provide the additional function of deep tissue coagulation or sterilisation in the scope instrument channel cleaning application or sterilisation of biological tissue in the NOTES or natural orifice application.

As with the dual functionality aspect discussed above, the plasma may be generated at the distal end of a flexible microwave cable with a diameter of less than 2.5 mm, which enables the instrument to be introduced down the instrument channel of any scoping device, i.e. endoscope, gastroscope, etc. It may also be used to clean or disinfect the instrument channel of endoscopes and be used to disinfect tissue before or after the treatment of ulcers, and/or to kill or reduce bacteria manifested in natural orifices of the body and/or to sterilise wound beds before skin grafts are performed and/or disinfect skin before it is grafted onto the body.

It may also be used in ear, nose and throat (ENT), in endometrioses procedures and general open procedures where it is necessary to prevent or stem blood flow/loss.

The present invention can be used in a number of open and endoscopic surgical applications where surface coagulation is beneficial, i.e. to stop superficial bleeding on the liver bed or breast flap surgery, to treat surface ulcers, etc. It may be particular useful in procedures that minimise bleeding in the upper and lower gastrointestinal tract, and it may play a part in the treatment for variceal bleeding and bleeding from peptic and duodenal ulcers, diverticulosis, angiodysplasia, colitis, colon carcinoma and anorectal disease.

BRIEF DESCRIPTION OF THE DRAWINGS

Embodiments of the invention are discussed below with reference to the accompanying drawings, in which:

FIG. 4A is a schematic cross-sectional view of an electrosurgical instrument that is an embodiment of the invention in a first configuration;

FIG. 4B is a transverse cross-section taken along the line B-B in FIG. 4A;

FIG. 4C is a schematic cross-sectional view of the electrosurgical instrument of FIG. 4A in a second configuration;

DETAILED DESCRIPTION; FURTHER OPTIONS AND PREFERENCES

Figure 1:
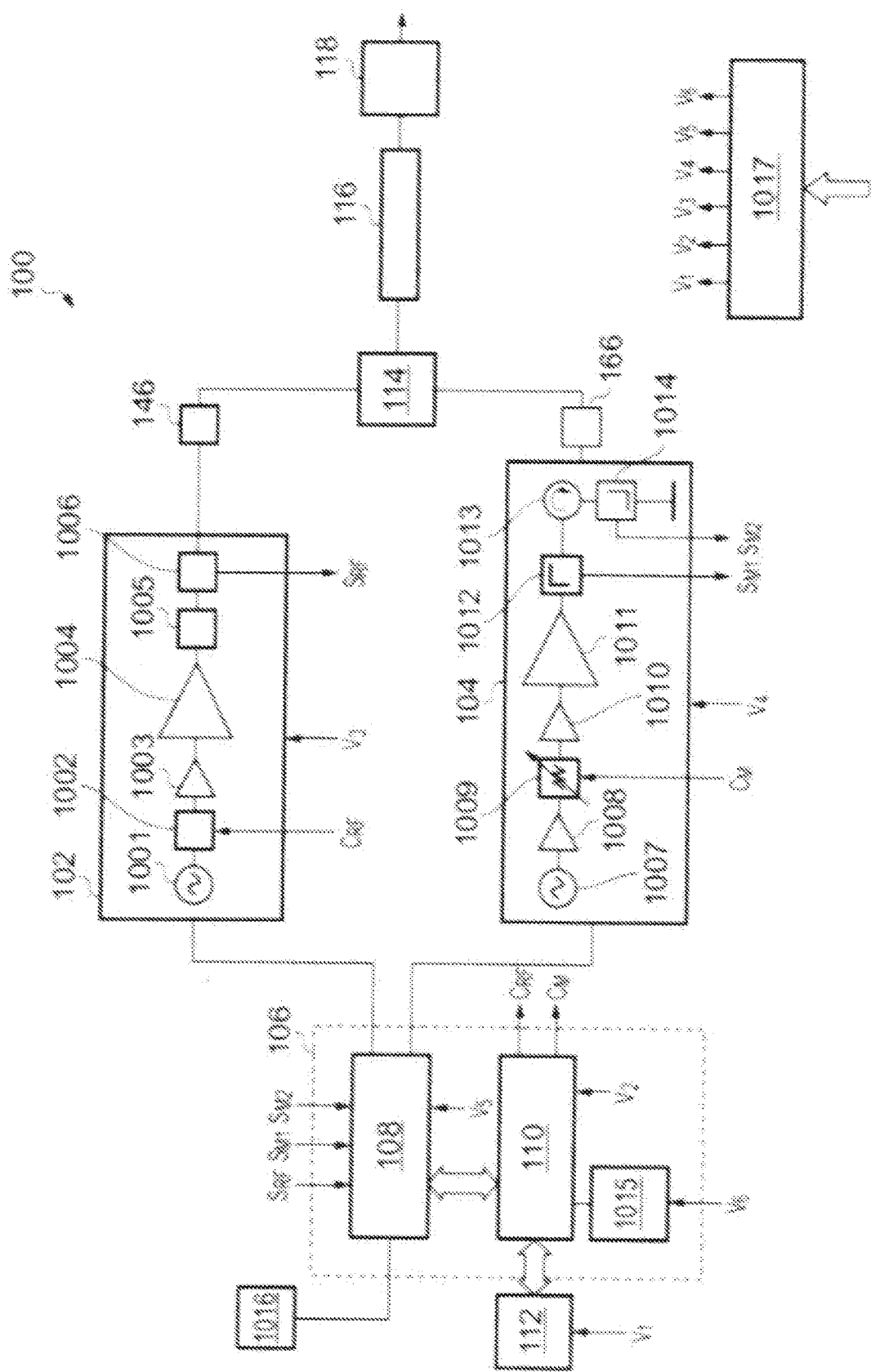
FIG. 1 is a known power delivery system suitable for use with the present invention.

FIG. 1 shows a schematic diagram of a power delivery system 100 disclosed in WO 2012/076844, which is suitable for use in the present invention.

The system 100 comprises an RF line-up 102 and a microwave line-up 104, which form parts of a RF channel and a microwave channel respectively.

The RF line-up 102 contains components for generating and controlling an RF frequency electromagnetic signal at a power level suitable for striking a plasma, as described below. In this embodiment, it includes an RF oscillator 1001, a power controller 1002, an amplifier unit (here comprising a driver amplifier 1003 and a power amplifier 1004), a transformer 1005 and an RF signal detector 1006.

The microwave line-up 104 contains components for generating and controlling a microwave frequency electromagnetic signal at a power level suitable for treating biological tissue. In this embodiment it includes a phase locked oscillator 1007, a signal amplifier 1008, an adjustable signal attenuator (e.g. an analogue or digital PIN diode based attenuator attenuator) 1009, an amplifier unit (here a driver amplifier 1010 and a power amplifier 1011), a forward power coupler 1012, a circulator 1013 and a reflected power coupler 1014. The circulator 1013 isolates the forward signal from the reflected signal to reduce the unwanted signal components present at the couplers 1012, 1014, i.e. it increases the directivity of the couplers. The circulator also protects the transistors within the high power output stage, e.g. the power GaN or GaAs transistors. It is preferable for the isolation between ports 1 to 3, 2 to 1 and 3 to 2 to be as high as possible, i.e. greater than 15 dB, or more preferably more than 20 dB.

The RF line-up 102 and microwave line-up 104 are in communication with a controller 106, which may comprise signal conditioning and general interface circuits 108, a microcontroller 110, and watchdog 1015. The watchdog 1015 may monitor a range of potential error conditions, which could result in the system not performing to its intended specification, i.e. the system delivers the wrong dosage of energy into patient tissue due to the output or the treatment time being greater than that demanded by the user. The watchdog 1015 comprises a microprocessor that is independent of the microcontroller 110 to ensure that microcontroller is functioning correctly. The watchdog 1015 may, for example, monitor the voltage levels from DC power supplies or the timing of pulses determined by the microcontroller 110. The controller 106 is arranged to communicate control signals to the components in the RF line-up 102 and microwave line-up 104. In this embodiment, the microprocessor 110 is programmed to output an RF control signal $C_{RF}$ and a microwave control signal $C_M$ for the power controller 1002 and the adjustable signal attenuator 1009 respectively. These control signals are used to set the energy delivery profile of the RF EM radiation and the microwave EM radiation output from the RF line-up 102 and microwave line-up 104 respectively. In particular, the power controller 1002 and the adjustable signal attenuator 1009 are capable of controlling the power level of the output radiation. Moreover, the power controller 1002 and the adjustable signal attenuator 1009 may include switching circuitry capable of setting the waveform (e.g. pulse width, duty cycle, and amplitude, etc.) of the output radiation.

The microprocessor 110 is programmed to output the RF control signal $C_{RF}$ and the microwave control signal $C_M$ based on signal information from the RF signal detector 1006 and forward and reflected power couplers 1012, 1014. The RF signal detector 1006 outputs a signal or signals $S_{RF}$ which are indicative of the voltage and current (and optionally the phase between the voltage and current) of the RF EM radiation on the RF channel. In this embodiment, the RF and microwave generator may be controlled by measurement of phase information only, which can be obtained from either the RF channel (from sampled current and voltage information) or the microwave channel (from sampled forward and reflected power information). The forward power coupler 1012 outputs a signal $S_{M1}$ indicative of the forward power level and the reflected power coupler 1014 outputs a signal $S_{M2}$ indicative of the reflected power level. The signals $S_{RF}$, $S_{M1}$, $S_{M2}$ from the RF signal detector 1006 and the forward and reflected power couplers 1012, 1014 are communicated to the signal conditioning and general interface circuits 108, where they are adapted to a form suitable for passing to the microprocessor 110.

A user interface 112, e.g. touch screen panel, keyboard, LED/LCD display, membrane keypad, footswitch or the like, communicates with the controller 106 to provide information about treatment to the user (e.g. surgeon) and permit various aspects of treatment (e.g. the amount of energy delivered to the patient, or the profile of energy delivery) to be manually selected or controlled, e.g. via suitable user commands. The apparatus may be operated using a conventional footswitch 1016, which is also connected to the controller 106.

The RF and microwave signals produced by the RF line-up 102 and microwave line-up 104 respectively are input to a signal combiner 114, which conveys the RF and microwave EM radiation separately or simultaneously along a cable assembly 116 to the probe 118. In this embodiment, the signal combiner 114 comprises a duplexer-diplexer unit that allows energy at microwave and RF frequencies to be transmitted along cable assembly 116 (e.g. a coaxial cable) to a probe (or applicator) 118, from which it is delivered (e.g. radiated) into the biological tissue of a patient into the instrument channel of a scope, e.g. an endoscope or another surface.

The signal combiner 114 also permits reflected energy, which returns from the probe 118 along cable assembly 116, to pass into the microwave and RF line-ups 102, 104, e.g. to be detected by the detectors contained therein. As explained below, the apparatus may include a low pass filter 146 on the RF channel and a high pass filter 166 on the microwave channel, so that only a reflected RF signal enters the RF line-up 102 and only a reflected microwave signal enters the microwave line-up 104.

Finally, the apparatus includes a power supply unit 1017 which receives power from an external source 1018 (e.g. mains power) and transforms it into DC power supply signals $V_1$-$V_6$ for the components in the apparatus. Thus, the user interface receives a power signal $V_1$, the microprocessor 110 receives a power signal $V_3$, the RF line-up 102 receives a power signal $V_3$, the microwave line-up receives a power signal $V_4$, the signal conditioning and general interface circuits 108 receives a power signal $V_5$, and the watchdog 1015 receives a power signal $V_6$.

Figure 2:
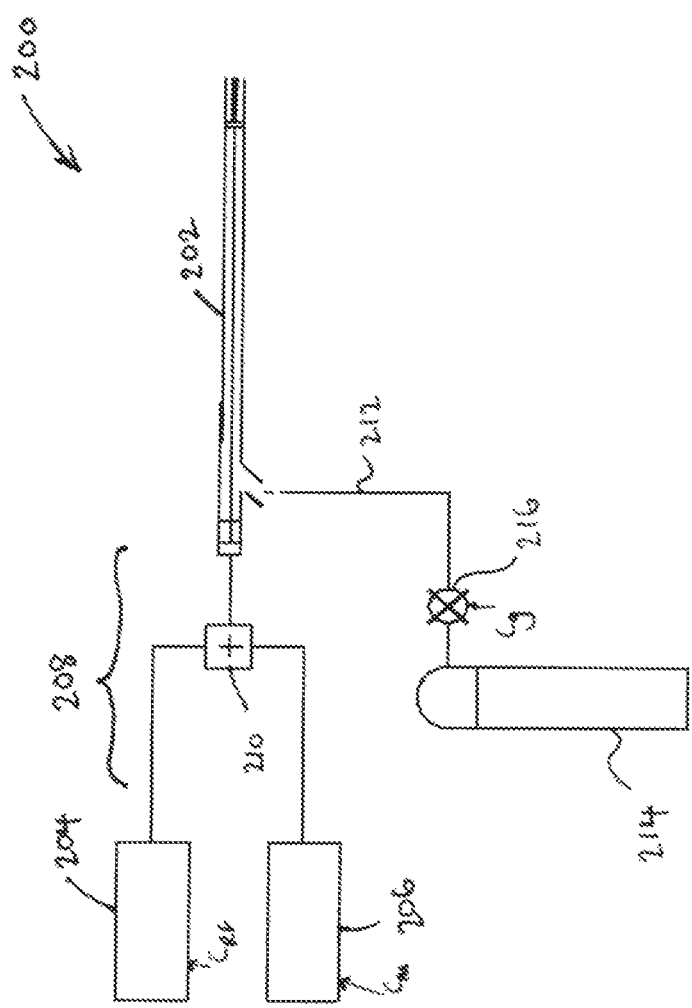
FIG. 2 is a schematic view of electrosurgical apparatus that is an embodiment of the invention.

FIG. 2 shows a schematic diagram of electrosurgical apparatus 200 that is an embodiment of the invention. The apparatus 200 comprises an electrosurgical instrument 202 capable of delivering plasma or non-ionising electromagnetic (EM) radiation from its distal end. Examples of the structure of the instrument 202 are described below.

The instrument 202 is connected to a power delivery system, which may be as described with reference to FIG. 1. However, in the embodiment of FIG. 2, the power delivery system comprises an radiofrequency (RF) radiation source 204 and a microwave radiation source 206 which are connected to deliver power to the proximal end of the instrument 202 via a feed structure 208. The feed structure 208 may include a signal combiner unit 210 as discussed above. The RF source 204 and the microwave source 206 may be arranged to output an RF signal and a microwave signal respectively based on control signals $C_{RF}$ and $C_M$ from a controller (not shown).

The instrument 202 is also connected to receive a gas, e.g. from a pressurised gas source 214 via supply line 212. A control valve 216 on the supply line 212 may be arranged to control the flow of gas received by the instrument 202, e.g. based on a control signal $C_g$ from the controller. It may be desirable to activate the gas control valve and/or flow controller prior to activating the RF and/or microwave energy sources in order to ensure that gas is present when said energy sources are activated as it is necessary for gas to be present in the plasma forming region before plasma can be generated. It may be preferable to include a gas sensor in the plasma forming region and the signals from this sensor used to control the gas flow valves. This system also helps control gas utilisation and prevents the patient from filling up with argon (or other) gas.

The RF and microwave measurement information may also be used to control the gas controller, i.e. the gas control valve may be closed when RF and/or microwave power cannot be detected using voltage/current and/or forward/reflected power monitoring circuits within the generator. It may be preferable to wait for a set period of time, i.e. 20 ms or 200 ms before shutting off the gas supply. This arrangement acts as a safety feature and as a means of controlling gas usage.

Figure 3A:
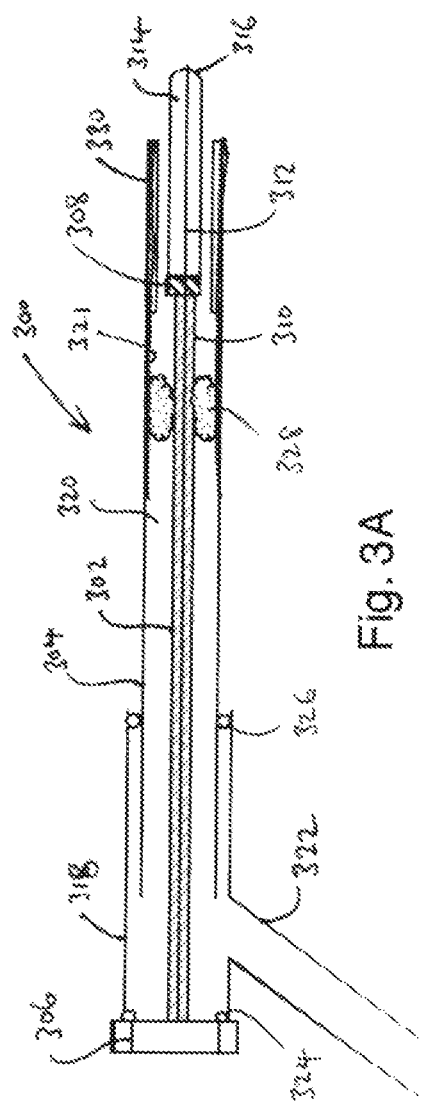
FIG. 3A is a schematic cross-sectional view of an electrosurgical instrument that is an embodiment of the invention in a first configuration.
Figure 3B:
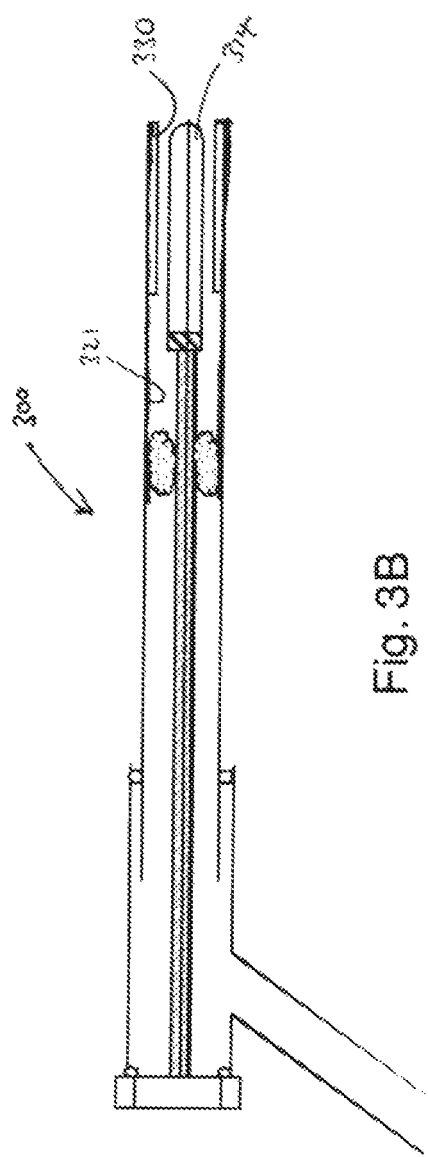
FIG. 3B is a schematic cross-sectional view of the electrosurgical instrument that of FIG. 3A in a second configuration.

FIGS. 3A and 3B shown a first embodiment of an electrosurgical instrument 300 according to the invention. The instrument 300 comprises an elongate probe made up of a central coaxial cable 302 surrounded by a tubular sleeve 304. The proximal end of the coaxial cable 302 (shown on the left in FIGS. 3A and 3B) terminates at a suitable connector 306 that is adapted to connect to the feed structure that supplied the RF and microwave signals. The coaxial cable 302 conveys the RF and microwave signals to the distal end of the instrument (on the right in FIGS. 3A and 3B).

The distal end of the coaxial cable 302 terminates at a insulating element 308 such as a glass bead or ceramic disc positioned between the body of the coaxial cable and the cylindrical cap to prevent shorting or breakdown from occurring. Alternatively, the dielectric within the microwave cable may extended by e.g. 0.1 mm to 0.2 mm past the outer conductor of the co-axial cable. The outer conductor 310 of the coaxial cable stops at the insulating element 308, but the inner conductor 312 continues through the insulating element 308 and protrudes beyond the insulating element 308 for a length selected (using simulations) to give best impedance match for deep coagulation. The protruding length is surrounded by a cylindrical ceramic (or other suitable dielectric or magnetic material) cap 314, which terminates at its distal end in a dome 316, e.g. a hemisphere. The inner conductor 312 protrudes slightly from the dome 316. The inner conductor 312 and cylindrical cap function as a first electrode of the instrument.

The sleeve 304 is a arranged to slide in a longitudinal direction relative to the coaxial cable 302. In this embodiment, the sleeve 304 is slidably mounted in a telescopic manner within a proximal base piece 318. A pull wire (not shown) may extend through the connector 306 to assist positioning of the sleeve 304 relative to the coaxial cable. The pull wire may be manually operated, or may be connected to an automated control mechanism, e.g. a stepper motor or linear motor, which can automatically control the position of the sleeve 304, e.g. on the basis of a control signal from the controller.

The pull wire may also take the form of a rigid section of tube connected to the co-axial cable at one end and arranged to slide over the sleeve (catheter). It may be preferable to introduce two catheter sections, a first section at the proximal end that is fixed to a 'Y' section (used to introduce the microwave/RF energy my means of a co-axial cable and the gas by means of a tube). The two inputs to the 'Y' piece and the common output must be sealed and be gas tight. A leur lock device with a circumferential seal that can be adjusted by tightening a thread may be used for this purpose. The first rigid section may slide over a second less rigid section (the main catheter) that is introduced inside the instrument channel of an endoscope or a cannula or the like. A seal is provided between the rigid proximal section and the flexible section to ensure that gas cannot escape at the interface between the two sections.

The sleeve 304 surrounds the coaxial cable 302 to define an annular space 320 between the outer surface of the coaxial cable 302 and the inner surface of the sleeve 304. Radial support elements or spacers (not shown) may be used to locate the coaxial cable 302 within the sleeve. The annular space 320 may be used to transport gas to the distal end of the instrument. The base piece 318 has a port 322 in a side surface thereof that is connected to the gas supply line. Gas tight seals 324, 326, which may be O-rings or the like, are provided at the join between the base piece 318 and the connector 306 and at the sliding junction between the base piece and sleeve 304 in order to minimise the escape of gas. Gas introduced into the port 322 therefore flows along the annular space 320 to exit the instrument at its distal end.

The sleeve 304 has an electrically conductive inner surface 321 along a length thereof leading up to its distal end. This electrically conductive inner surface 321 is electrically connected to the outer conductor 310 of the coaxial cable 302. In this embodiment, this is done by means of an electrically conductive mesh 328 mounted within the annular space 320. The mesh is porous, and therefore permits the gas to flow through it whilst also providing an electrical connection. This could also be achieved using a spring or a plurality of small wires electrically connected, i.e. soldered or crimped or trapped, to one or both surfaces of conductors or electrodes 310 and 321. Providing at least two, ideally at least four, circumferential contact points around the circumference of the conductor(s) can ensure good enough electrical contact for the microwave energy to propagate unimpaired. It may also be possible and preferable to put a plurality of dents or a partial crimp (e.g. 180°) in/on one of the conductors in order to make the necessary electrical contact needed whilst also enabling the gas to flow onto the plasma generating region or the distal end of the device where plasma is formed.

The electrically conductive inner surface 321 of the sleeve is further covered by an insulating tube 330 (e.g. made of quartz, ceramic or the like) along a distal length thereof that can overlap longitudinally with the cylindrical cap 314. The electrically conductive inner surface 321 and insulating tube 330 function as a second electrode of the instrument.

The slidable sleeve permits the instrument to adopt two configurations. In a first configuration, as shown in FIG. 3B, the electrically conductive inner surface 321 of the sleeve 304 is longitudinally in line with the cylindrical cap 314. This configuration sets up a region of high impedance which exhibits a high electric field when the RF or microwave signal is supplied to the instrument. In this configuration, the instrument may be adapted to deliver plasma, e.g. thermal plasma for surface coagulation or non-thermal plasma for sterilisation, from the distal end of the probe.

The microprocessor may be arranged to output a control signal to adjust the position of the sliding sleeve relative to the coaxial cable based on the detected return loss or impedance mismatch that is determined in the controller from the microwave detection signal. This control may be done when plasma is being generated e.g. to maintain a pre-set required match or return loss, e.g. 10 dB (90% of the microwave energy is delivered into the plasma).

In a preferred embodiment, the plasma (thermal or non-thermal as required) is generated by the follow steps:
supply gas to the distal region of the instrument (i.e. to the region between the quartz tube 330 and cylindrical cap 314),
sending a pulse of RF energy through the coaxial cable to strike a plasma in the gas at the distal region by generating a high electric field in the region, and
sending a pulse of microwave energy through the coaxial cable to sustain or maintain the plasma to ensure that appropriate treatment takes place.

The RF pulse may be automatically triggered by a characteristic (e.g. the rising edge) of the microwave pulse, so that the strike and sustain pulses are always synchronised. The RF pulse is arranged to have a voltage suitable for setting up an electric field for striking the plasma. The voltage may be between 150 V and 1500 V peak, more preferably between 250 V and 750 V peak. The frequency of the RF pulses may be between 100 kHz and 1 MHz, where a the window or burst of sinusoidal waveform or signals is gated (based on the detected microwave pulse) and is preferably between 0.5 μs and 10 ms.

The delivered microwave power may be monitored (e.g. by measuring forward and reflected microwave signals) in order to check the status of the plasma.

In the embodiment above, the plasma is struck by the RF signal. In other embodiments, the plasma may be struck by the microwave signal only, because the close proximity between the inner and outer conductors enables a high electric field to be generated from the microwave signal. For example, if it is possible to deliver 25 W of CW microwave power to the distal end of the instrument then this may create a high enough electric field. One possible means of striking plasma using the microwave field is to decrease the distance between the two conductors within the plasma generating region at the time plasma is struck and then increase the distance again once it has been struck in order to create the optimal environment (impedance) for plasma to be sustained. In this configuration, the adjustable sleeve (outer tube) may be arranged to be or set up to be in four possible positions, which are as follows:

Position 1—monopole radiating antenna exposed to deliver non-ionising microwave radiation for deep coagulation;

Position 2—Plasma generating region set up, radiating monopole is covered by outer sleeve and gas is introduced into the region so that plasma (thermal for surface coagulation and/or non-thermal for sterilisation/disinfection) can be struck and sustained using RF and microwave energy respectively;

Position 3—Plasma is struck using microwave energy and the proximity between the inner and outer conductors is adjusted generate a high enough E-field to strike plasma;

Position 4—Plasma is sustained using the microwave field and the proximity between the inner and outer conductors is adjusted generate a low impedance environment to allow plasma to be sustained.

The control of the position of the sleeve and the formation of the various regions may be carried out automatically based on movement of a linear actuator or a stepper motor based on voltage and/or current signals from the RF channel and/or forward and/or reflected power signals from the microwave channel.

If the coaxial section that includes the insulating tube 330 and cylindrical cap 314 has an impedance of 50 ohms, then the peak voltage will be 50 V, which produces an electric field of 50 kV/m if the distance between the inner conductor 312 and the electrically conductive inner surface of the sleeve 304 conductor is 1 mm. Such a field may be capable of striking a plasma if argon was present in the gap. It may also be possible to switch in an impedance transformer, i.e. a quarter wave transformer, to produce a the necessary voltage increase needed to strike plasma, e.g. a quarter wave line with an impedance of 250Ω with a 50Ω source impedance and a power source of 25 W, will produce a strike voltage of:

$$\sqrt{\left(\frac{(250)^2}{50} \times 25\right)} = 177 \text{ V}.$$

In such embodiments, the instrument may only receive a microwave input; the power delivery system need not have an RF source in this arrangement.

In a second configuration, as shown in FIG. 3A, the sleeve 304 is slid back relative to the coaxial cable 302 to expose a length of the cylindrical cap 314 at the distal end of the device. The exposed end functions as a radiating monopole microwave antenna. In this configuration, a microwave signal is supplied to the coaxial cable in the absence of gas. The microwave signal is emitted at a non-ionising radiation field to perform deep tissue coagulation. The levels of non-ionising microwave power delivered at the distal radiating monopole may be between 2.5 W and 50 W continuous wave power; the level is dependent on the rate of blood flow or the size of the vessel being coagulated. The power level also depends on the properties of the microwave transmission cable used to deliver the microwave energy from the generator to the applicator or antenna.

FIGS. 4A, 4B and 4C show a second embodiment of an electrosurgical instrument 400 according to the invention. Common features with FIGS. 3A and 3B are given the same reference numbers. The second embodiment is similar to the first embodiment except for the way in which the outer conductor 310 of the coaxial cable 302 is electrically connected to the electrically conductive inner surface 321 of the sleeve 304. Instead of conductive mesh, the second embodiment using a split conical member 402 made of electrically conductive material to connect the outer conductor 310 of the coaxial cable 302 to the electrically conductive inner surface 321 of the sleeve 304. The conical member 402 comprises a plurality of fingers which flare out from the coaxial cable towards the sleeve 304. The sleeve 304 may slide relative to the fingers, or the conical member 402 may be fixed to the sleeve and slide over the coaxial cable.

FIG. 4B shows a cross-sectional view through the split conical member 402, which shows how the gas can pass between the fingers to reach the distal end of the probe.

FIG. 4C shows the instrument in the first configuration and FIG. 4A shows the instrument in the second configuration, as discussed above.

Figure 5:
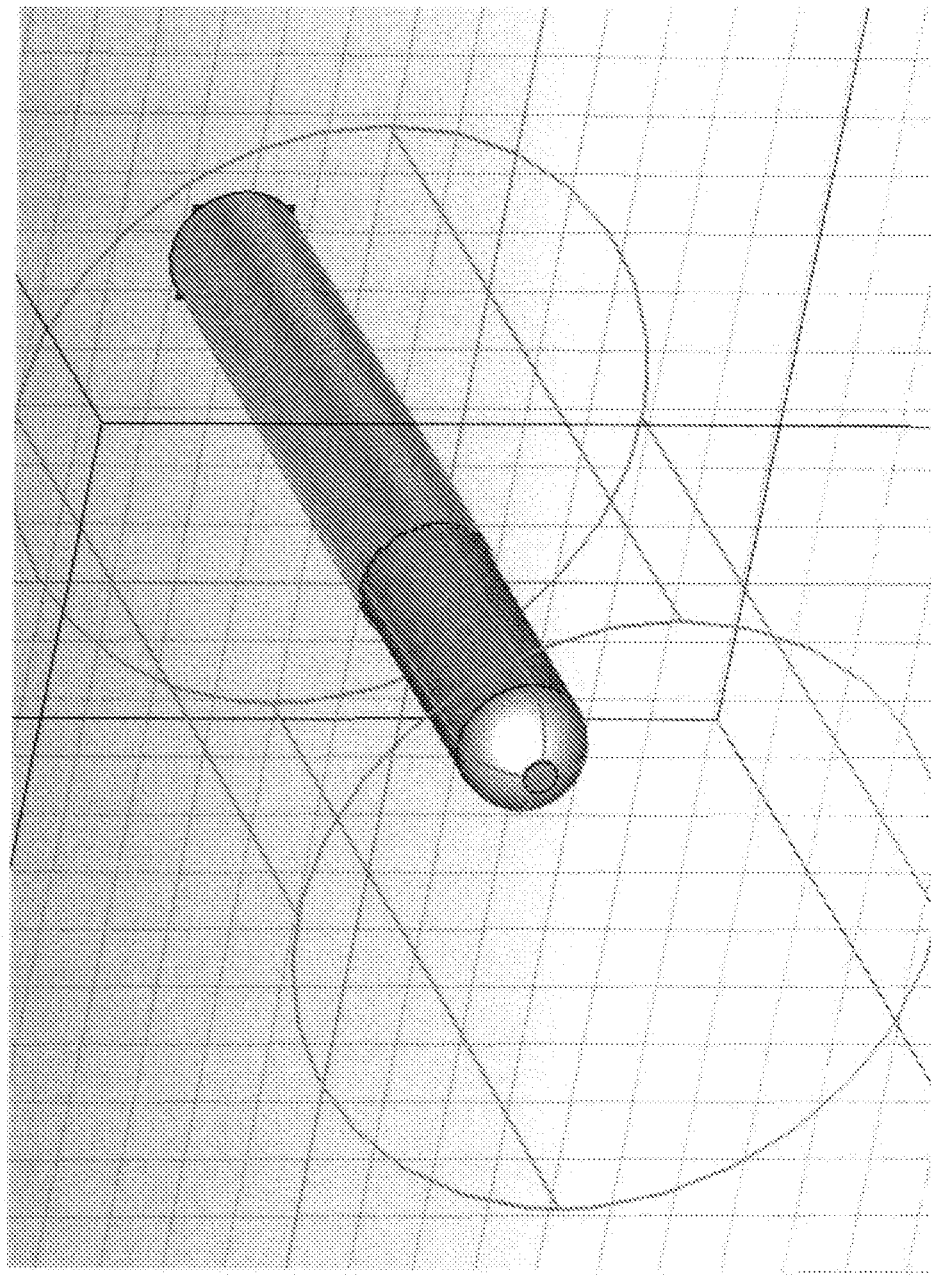
FIG. 5 is a perspective view of the dielectric cylinder used to model the first electrode of an electrosurgical instrument that is an embodiment of the invention.
Figure 6A:
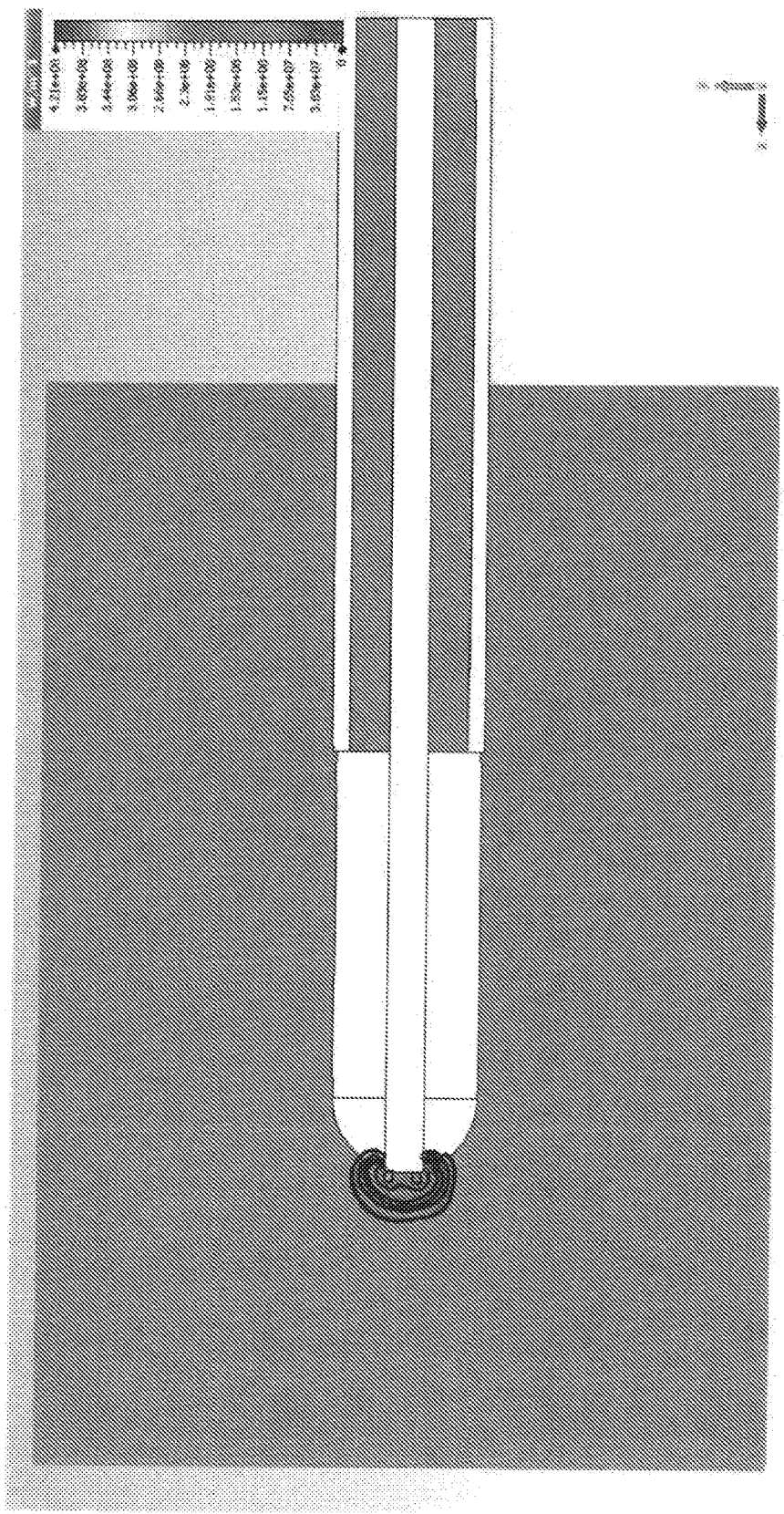
FIGS. 6A and 6B are microwave field simulations of the first electrode shown in FIG. 5 with power delivered into representative models of blood and liver tissue.
Figure 6B:
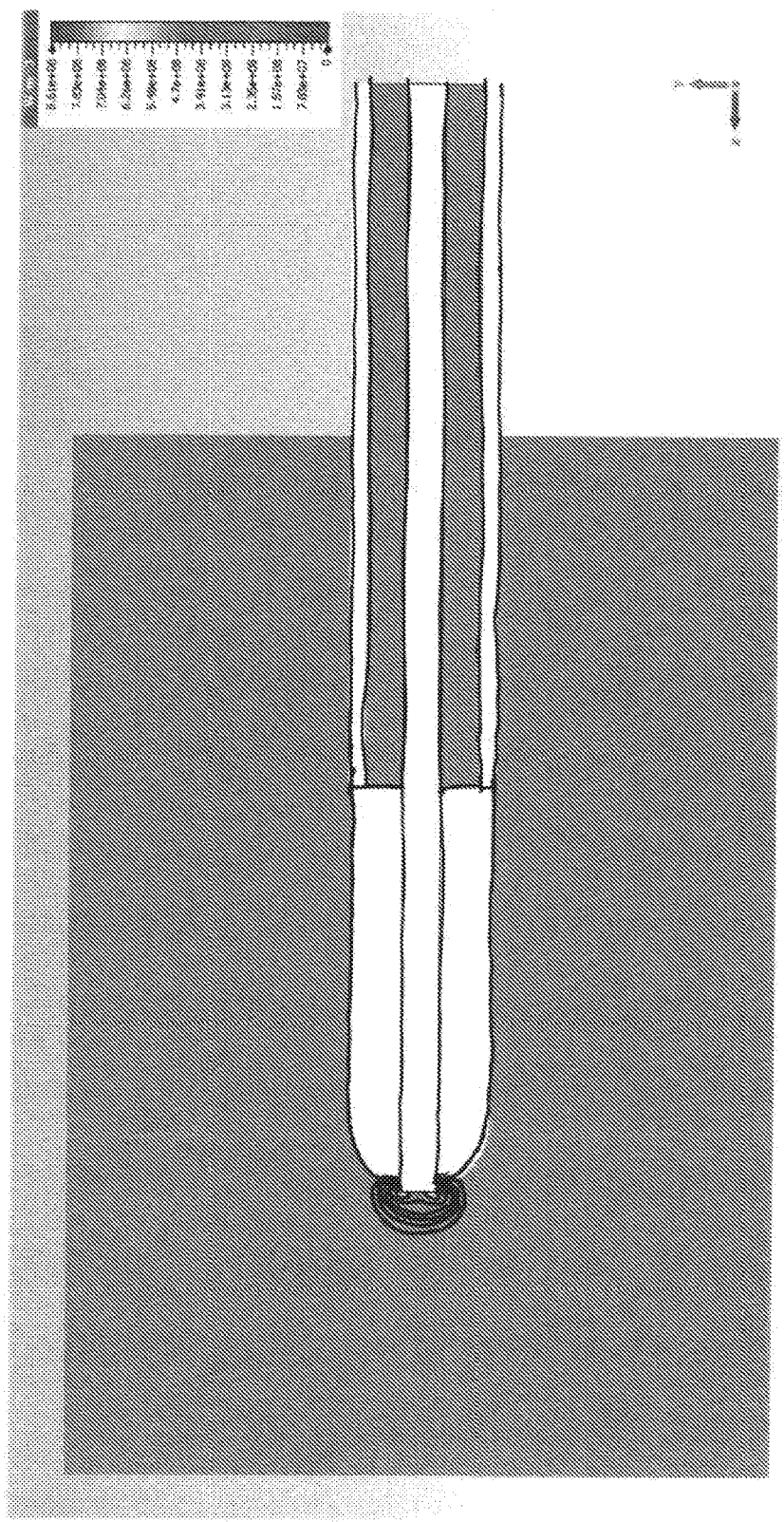
Figure 6C:
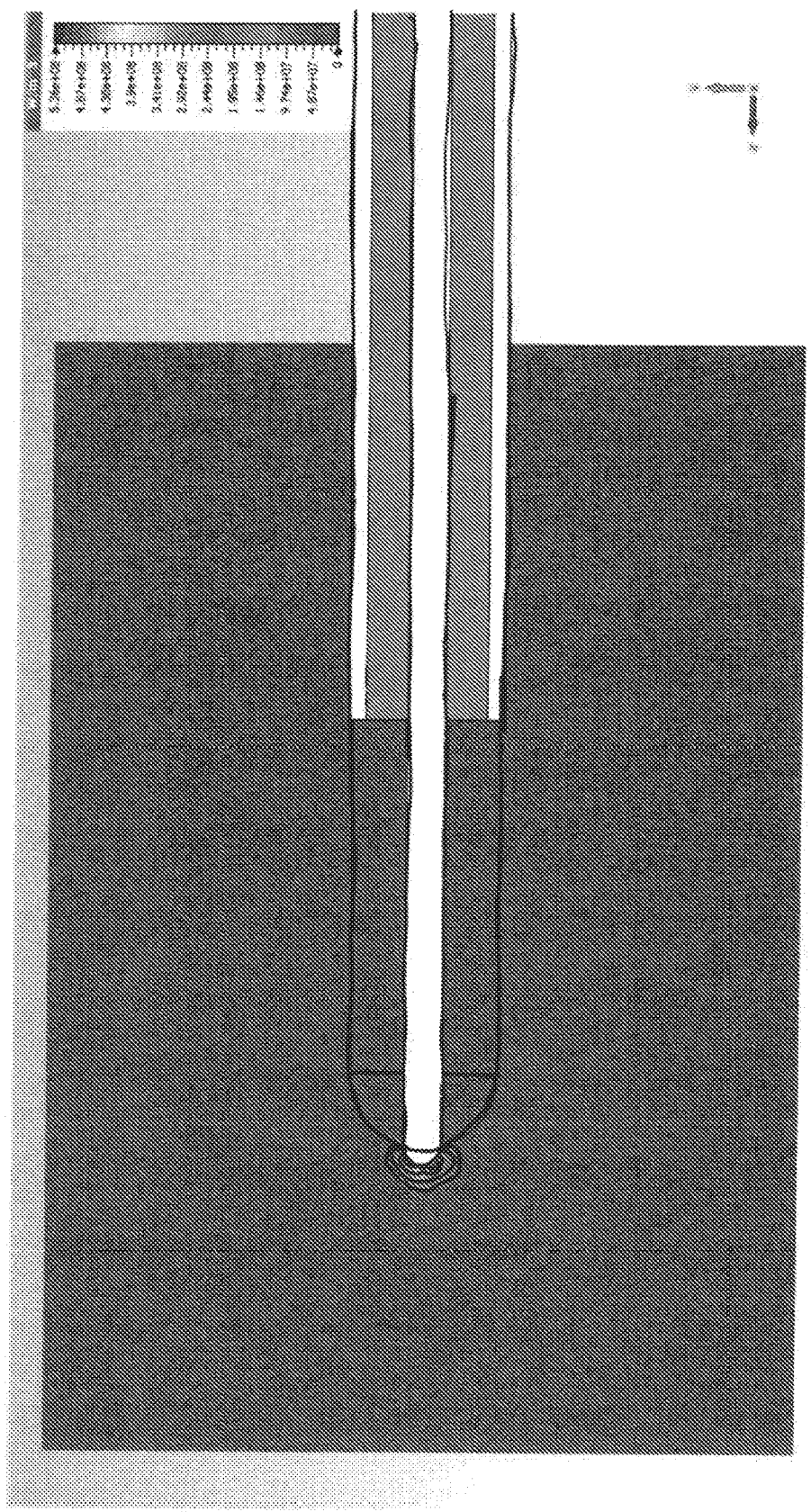
FIG. 6C is a microwave field simulation of the first electrode shown in FIG. 5 with a rounded inner conductor termination into the liver model.

FIG. 5 is a perspective view of a dielectric cylinder used to model the cylindrical cap that forms part of the first electrode of an electrosurgical instrument described above. It has been found that a rounded cylinder having a diameter of around 2 mm and a length of 6.7 mm gives a good match into liver tissue for the microwave power at 5.8 GHz, and therefore is useful for the efficient delivery of energy in the deep coagulation mode (i.e. the second configuration). As shown in FIGS. 6A to 6C, the heating produced by the non-ionising radiation emitted from this structure is over a very small region about 1 mm radius centred on the end of the inner conductor. FIGS. 6A and 6B show the inner conductor terminating at a flat surface with sharp edges. The fields are very high at the sharp edges. FIG. 6C shows the inner conductor terminating in a dome (e.g. hemisphere), which causes the fields to be more even.

Figure 7A:
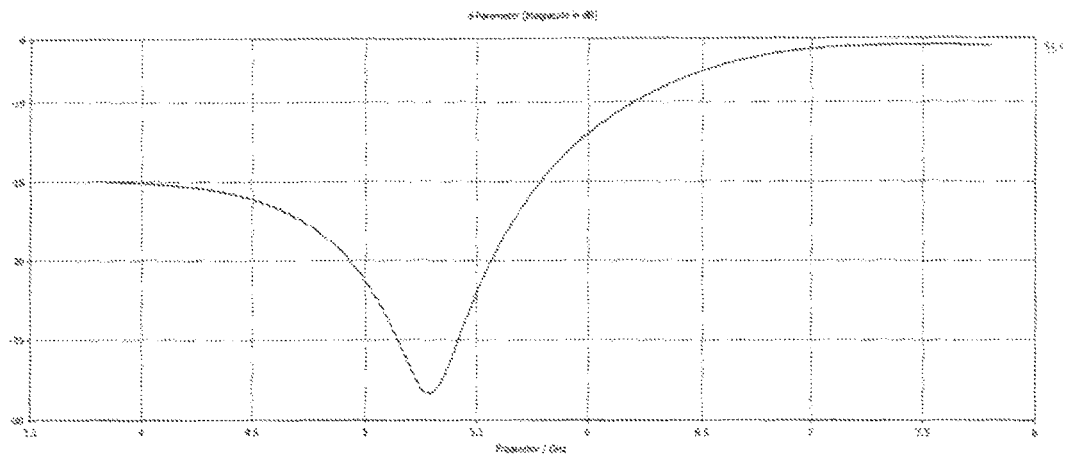
FIGS. 7A and 7B are plots showing simulated return loss for the structures of FIGS. 6A and 6C into representative models of blood and liver tissue respectively.
Figure 7B:
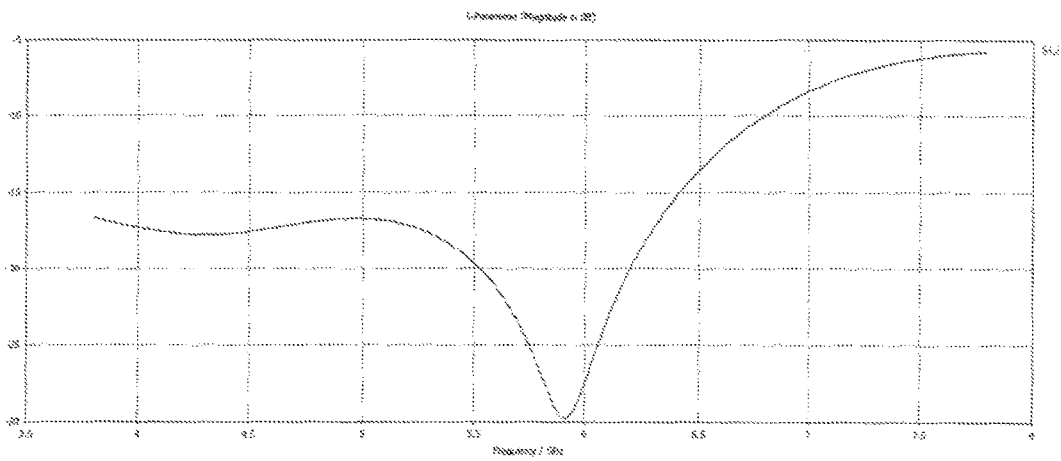

FIGS. 7A and 7B show a plot of the return loss for the structures in FIGS. 6C and 6B respectively. In general they demonstrate a good match into tissue around the frequency used for the microwave signal in this embodiment (5.8 GHz). FIG. 7A shows that a hemispherical end on the inner conductor lowers the matched frequency, but this can be easily adjusted by shortening the length of the cap.

Figure 8A:
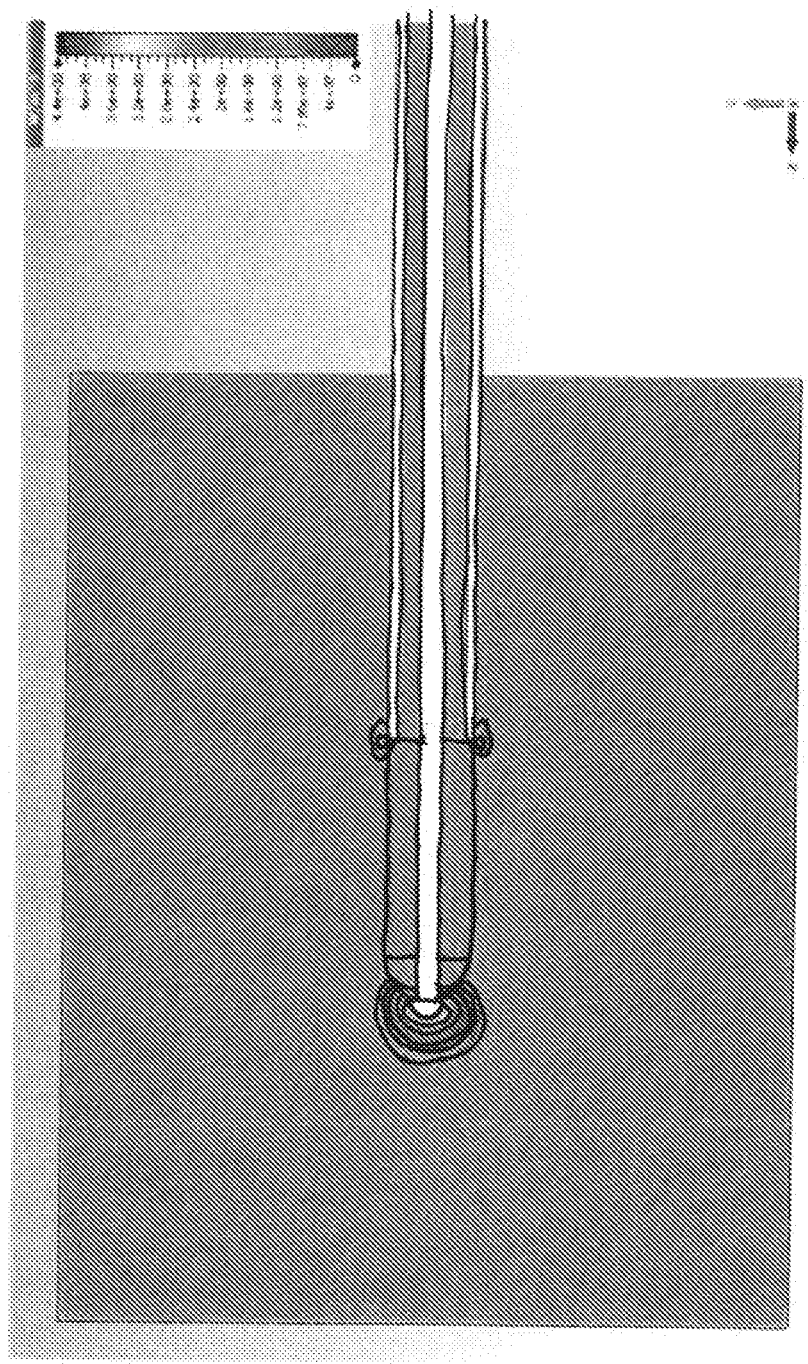
FIGS. 8A and 8B are microwave field simulations of another first electrode into representative models of blood and liver tissue.
Figure 8B:
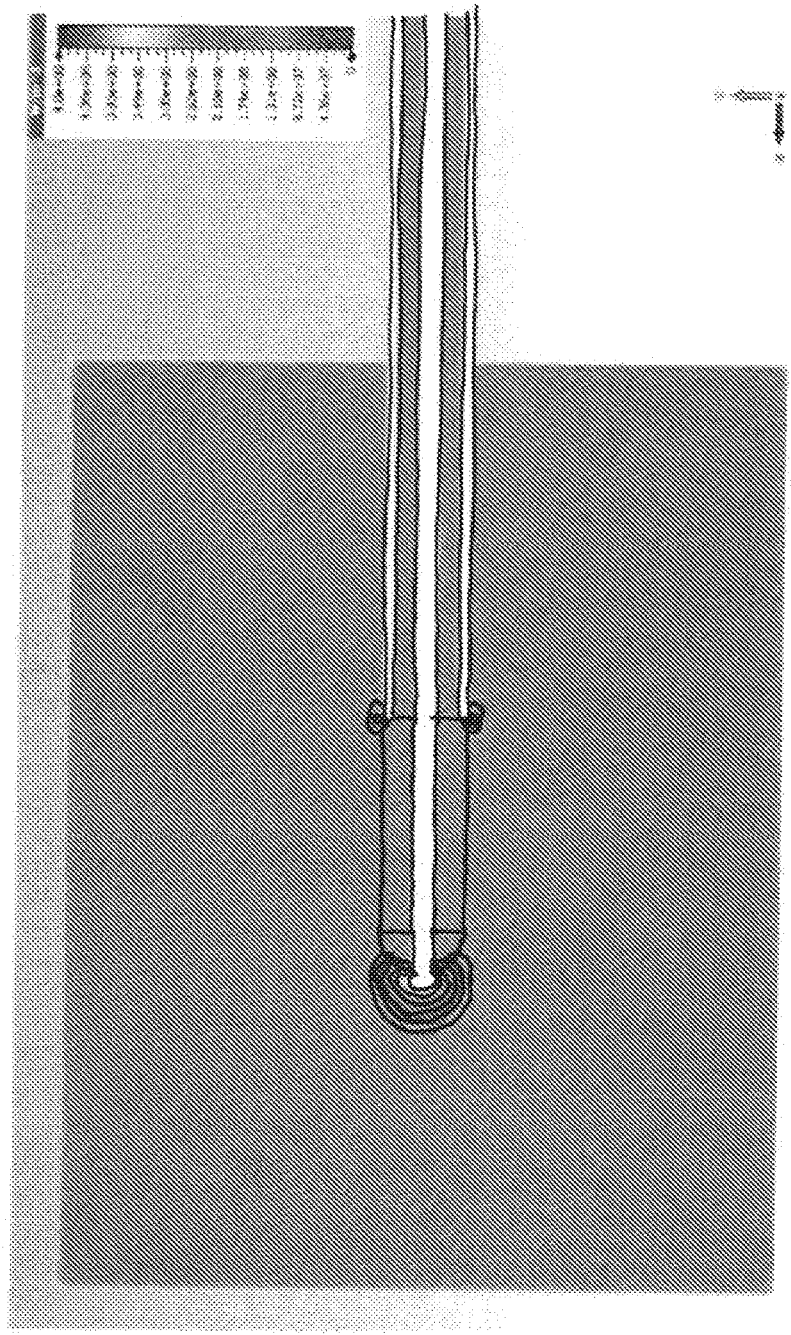

FIGS. 8A and 8B are microwave field simulations of a cylindrical cap terminating at the distal end of Sucoform 86 microwave cable from Huber & Suhner or the like (i.e. a 2.2 mm diameter cable) into blood and liver tissue respectively. In this arrangement, the material used for the cylindrical cap is PEEK, and the length of the cylindrical section before the hemisphere was 3 mm. Thus, the cap (e.g. made of PEEK) has a diameter of 2 to 2.1 mm and a total length of 4 to 4.1 mm. In this arrangement, the dome at the end of the inner conductor is modelled with a 1 mm diameter. Again the heating from such structure is localised around the distal tip.

Figure 9A:
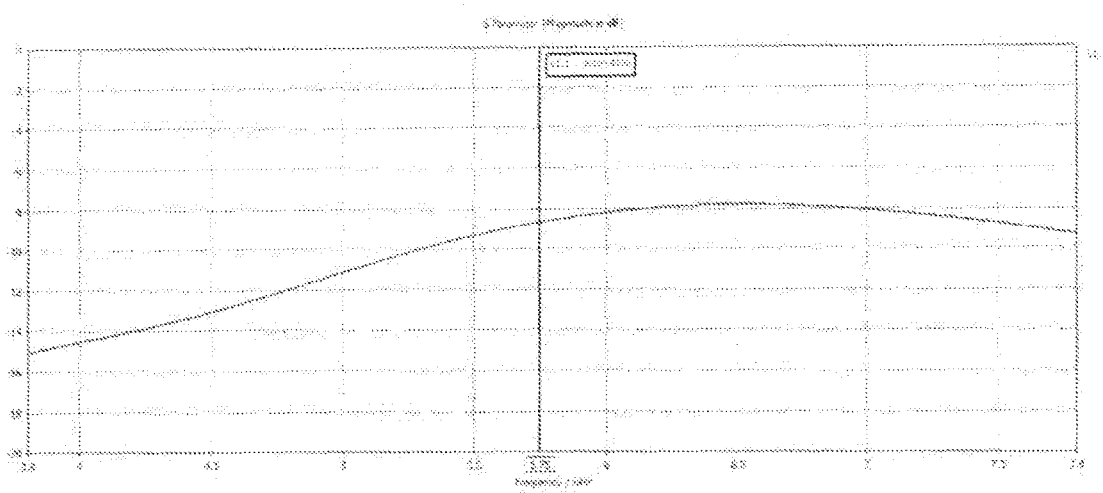
FIGS. 9A and 9B are plots showing simulated return loss for the structures of FIGS. 8A and 8B into representative models of blood and liver tissue respectively.
Figure 9B:
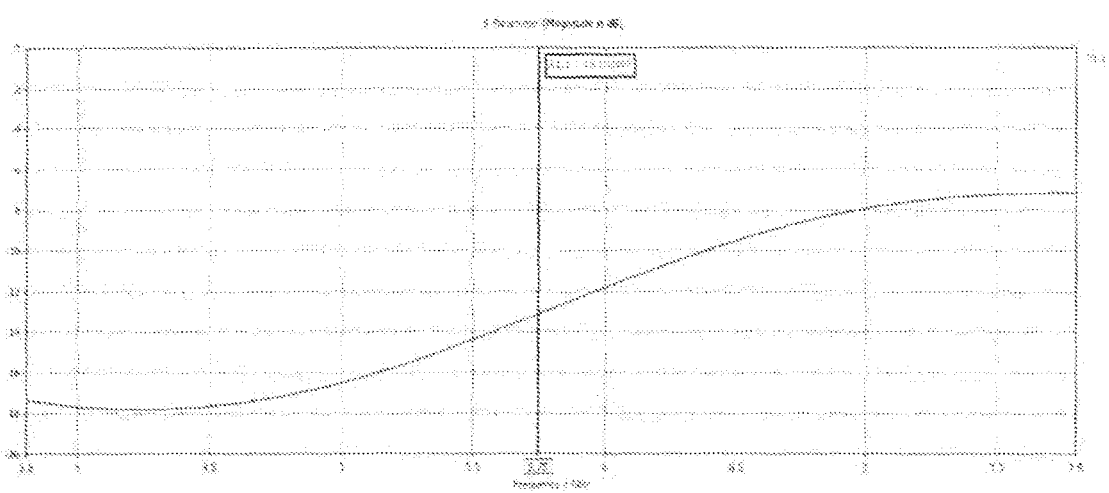

FIGS. 9A and 9B show a plot of the return loss for the structures in FIGS. 8A and 8B respectively. The losses at the frequency of interest here (around 5.8 GHz) are acceptable.

Figure 10:
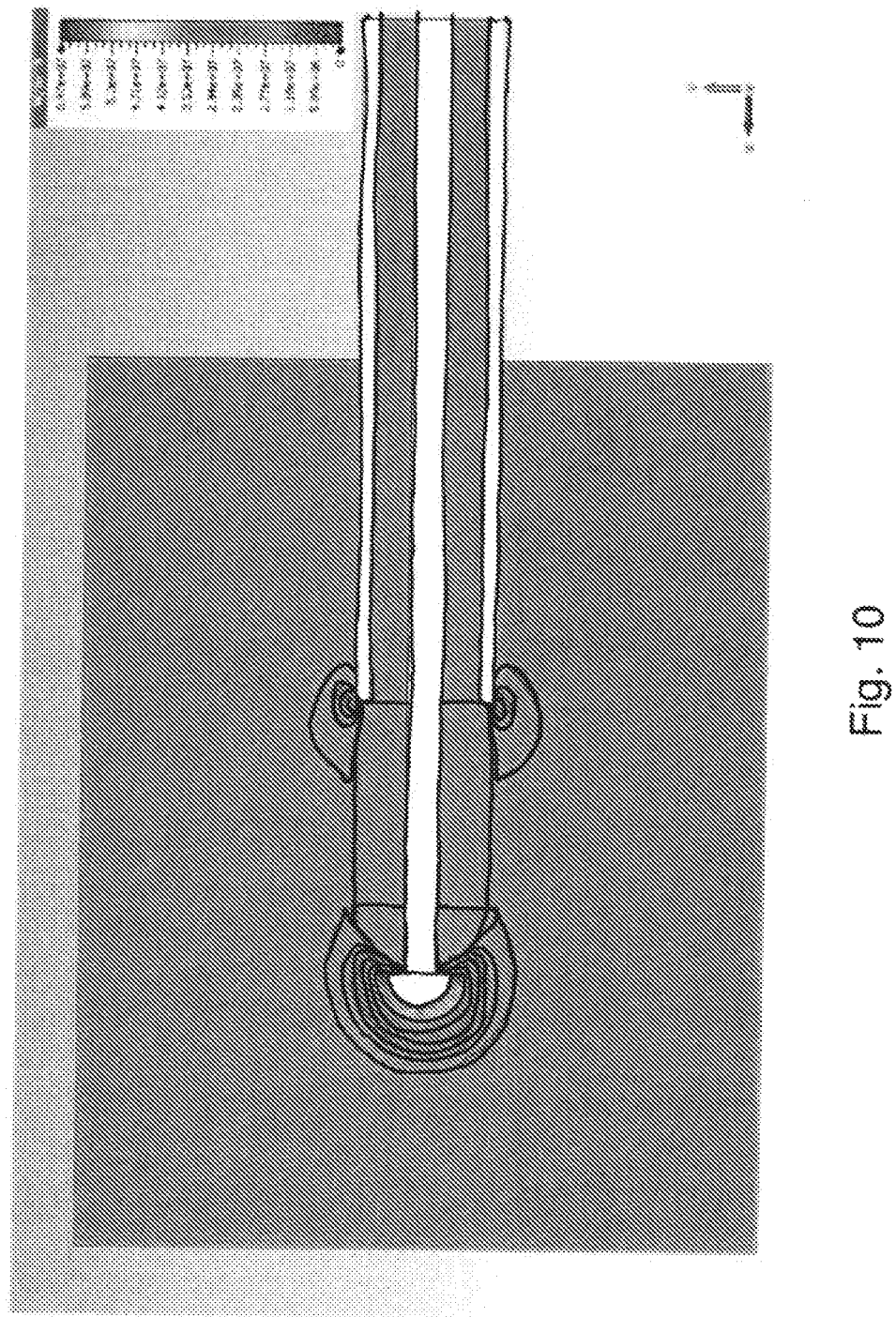
FIG. 10 is a microwave field simulation of another first electrode into blood and liver tissue.

FIG. 10 is a microwave field simulation of a cylindrical cap terminating at the distal end of Sucoform 47 microwave cable from Huber & Suhner or the like (i.e. a 1.2 mm diameter cable) into liver tissue. In this arrangement, the material used for the cylindrical cap is also PEEK, and the length of the cylindrical section before the hemisphere was also 3 mm. However, the diameter of the cap in this arrangement is 1.2 mm and therefore has a total length of about 3.6 mm. In this arrangement, the dome at the end of the inner conductor is modelled with a 0.5 mm diameter.

Figure 11A:
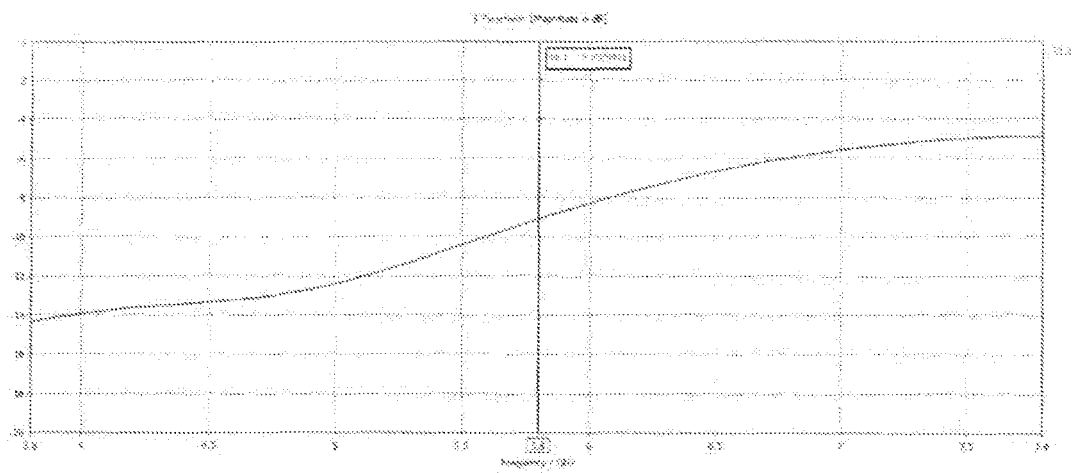
FIGS. 11A and 11B are plots showing simulated return loss for the structure of FIG. 10 into representative models of blood and liver tissue respectively.
Figure 11B:
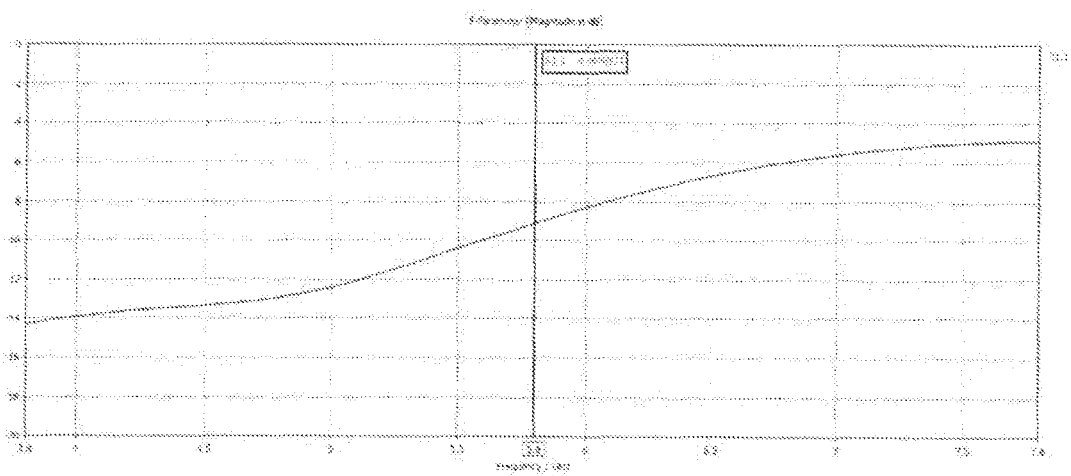

FIGS. 11A and 11B show a plot of the return loss for the structures of FIG. 10 into blood and liver tissue respectively. Again, the losses at the frequency of interest here (around 5.8 GHz) are acceptable.

Figure 12A:
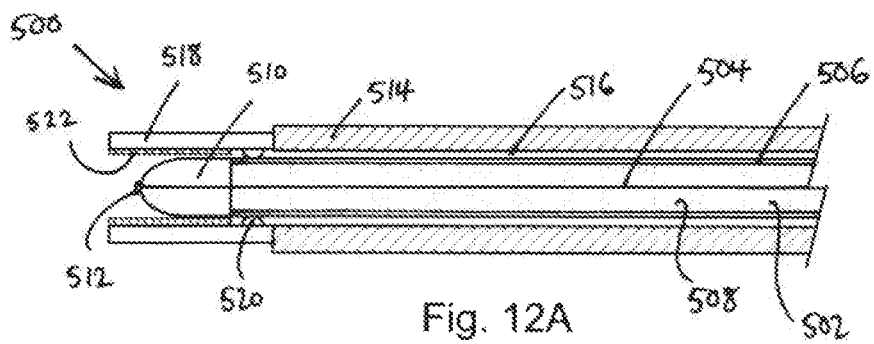
FIGS. 12A and 12B are schematic cross-sectional views of an electrosurgical instrument that is yet another embodiment of the invention.
Figure 12B:
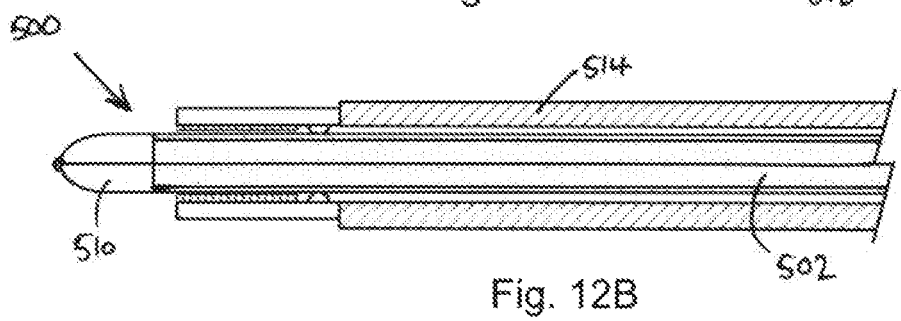

FIGS. 12A and 12B show a schematic cross-sectional view through an electrosurgical instrument 500 that is an embodiment of the invention, which utilises the microwave emitting structures discussed above with reference to FIGS. 6 to 11.

FIG. 12A shows the electrosurgical instrument 500 in a first configuration that is suitable for delivering a plasma at the distal end. The instrument 500 is cylindrical, and sized to fit down the instrument channel of a scoping device, e.g. an endoscope. The instrument comprises a coaxial cable 502 having an inner conductor 504 and an outer conductor 506 separated from the inner conductor 504 by a dielectric material 508. The outer conductor 506 is exposed around at the outside surface of the coaxial cable 502. At the distal end of the coaxial cable 502, the inner conductor 504 extend beyond the outer conductor 506 and its surrounding by a dielectric cap 510, e.g. made of PEEK or the like. The cap 510 is a cylinder having substantially the same diameter as the coaxial cable 502. The distal end of the cap 510 forms a rounded, e.g. hemispherical dome. The inner conductor 504 terminates at its distal end is a rounded tip 512 which projects beyond the end of the cap 510.

The coaxial cable 502 is mounted within a sleeve 514, which preferably includes internal braids (not shown) to impart strength. There is an annular gap 516 between the inner surface of the sleeve 514 and the outer surface of the coaxial cable 502 (i.e. the exposed outer conductor) which forms a gas flow path for conveying gas introduces at the proximal end of the sleeve 514 to the distal end.

A conductive terminal tube 518 is mounted at the distal end of the sleeve 514. For example, the conductive terminal tube 518 may be welded to the sleeve 514. In the configuration shown in FIG. 12A, the rounded tip 512 of the inner conductor 504 forms a first electrode and the conductive terminal tube 518 forms a second electrode. An electric field for striking a plasma in the gas flowing from the annular gap 516 is formed between the first electrode and second electrode by applying suitable energy (e.g. RF and/or microwave frequency energy) to the coaxial cable, as explained above.

The conductive terminal tube 518 is electrically connected to the outer conductor 506 of the coaxial cable 502 by a plurality of radially projecting bumps 520 on the inner surface of the conductive terminal tube 518. There may be two, three, four or more bumps 520 spaced from one another around the inner circumference of the conductive terminal tube 518. Spacing the bumps in this manner permits the gas to flow past.

An insulating liner 522 is mounted around the inside surface of the conductive terminal tube 518 along a distal length thereof. The insulating liner 522 may be made of polyimide or the like. The purpose of the liner 522 is to provide a suitable dielectric barrier between the first electrode and second electrode to ensure that the applied RF and/or microwave frequency energy results in an electric field with high voltage for striking the plasma. There is a small gap between the liner 522 and the cap 510 to permit the gas to flow past.

FIG. 12B shows the electrosurgical instrument 500 in a second configuration that is suitable for delivering non-ionising microwave frequency energy at its distal end. In this configuration, the cap 510 extends out of the conductive terminal tube 518, where it forms a monopolar microwave antenna as discussed above.

To transform the instrument 500 between the first configuration and the second configuration, the coaxial cable 502 slides axially relative to the sleeve 514. The sliding operation may be effected by a physical slider switch mounted on a proximal handpiece of the instrument, where it may be operated by the surgeon.

Figure 13:
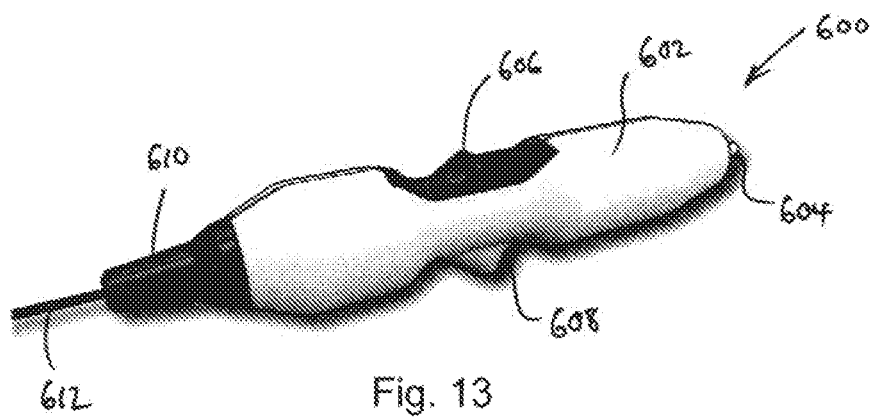
FIG. 13 is a perspective view of a handpiece suitable for operating the electrosurgical instrument of the invention.

FIG. 13 shows a perspective view of a handpiece 600 that may be used with or form part of the electrosurgical instrument that is an embodiment of the invention. The handpiece comprises a housing 602 or shell for surrounding and protecting the inner components. The housing has a proximal port 604 at its back end for connecting to a coaxial cable to receive RF and/or microwave frequency energy from an electrosurgical generator (not shown). In a middle portion of the housing 602 there is a slider switch 606 for changing the configuration at the distal end of the instrument. On an opposite side of the housing from the slider switch 606 there is a gas receiving port 608 for attaching to a suitable gas feed pipe (not shown). At the distal end of the housing 602 there is a flexible nozzle 610 which acts as a protective guide for the sleeve 612 that conveys the gas and energy to the treatment location.

Figure 14:
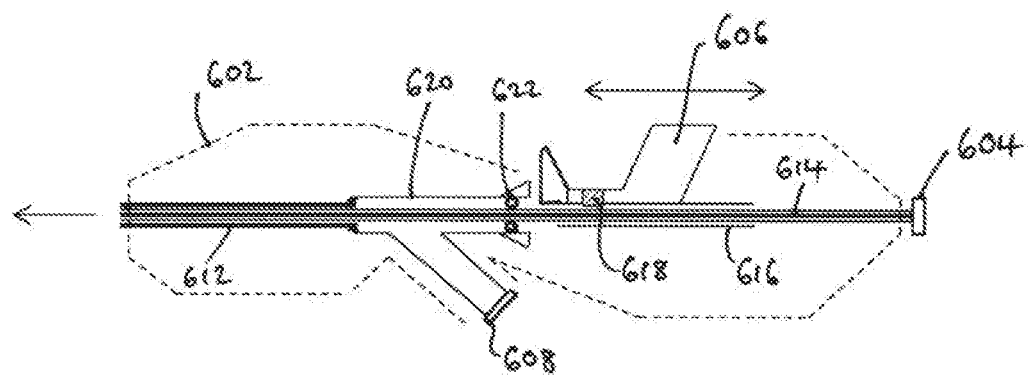
FIG. 14 is a schematic cross-section view through the handpiece shown in FIG. 13.

FIG. 14 shows a cross-sectional view of the inner components of the housing 602. A coaxial cable 614 extends through the housing from the proximal port 604. A collar 616, e.g. of stainless steel is mounted on (e.g. soldered to) the coaxial cable 614 at a proximal end thereof. The slider switch 606 is attached to the collar 616 via a grub screw 618. This arrangement ensures that the slider switch 606 can be securely attached to the coaxial cable without damaging it.

The coaxial cable 614 is received in a first input port of a Y-shaped junction 620. The second input port of the Y-shaped junction 620 is connected to the gas receiving port 608. Gas introduced into the Y-shaped junction 620 is prevented from escaping through the first input port by a suitable seal 622.

The coaxial cable 614 extends through the Y-shaped junction 620 and exits it at an output port. A proximal end of the sleeve 612 is secured (e.g. adhered) to the output port of the Y-shaped junction 620, where it receives both gas from the gas receiving port 608 and the coaxial cable. In use, the slider switch 606 is movable relative to the housing 602 to extend and retract the coaxial cable 614 within the sleeve 612. The movement range of the slider switch may be 20 mm.

The invention claimed is:

1. An electrosurgical instrument comprising:
   an elongate probe comprising a coaxial cable for conveying radiofrequency (RF) and/or microwave frequency electromagnetic (EM) energy, and a probe tip connected at a distal end of the coaxial cable for receiving the RF and/or microwave energy; and
   a gas passage for conveying gas through the elongate probe to the probe tip,
   wherein the coaxial cable comprises an inner conductor, an outer conductor and a dielectric material separating the inner conductor from the outer conductor,
   wherein the probe tip comprises a first electrode connected to the inner conductor of the coaxial cable and a second electrode connected to the outer conductor of the coaxial cable, and
   wherein the first electrode and second electrode are movable relative to each other between:
      a first configuration in which they are arranged to produce an electric field from the received RF and/or microwave frequency EM energy across a flow path of gas from the gas passage to produce a thermal or non-thermal plasma, and
      a second configuration in which the first electrode extends distally beyond the second electrode to form a radiating structure for emitting a microwave EM field outwardly from the probe tip.

2. An electrosurgical instrument according to claim 1, wherein the elongate probe comprises a sleeve surrounding the coaxial cable, the gas passage being a space between an inside surface of the sleeve and an outside surface of the coaxial cable.

3. An electrosurgical instrument according to claim 2, wherein the second electrode is formed on a distal end of the sleeve, and the sleeve is retractable relative to the coaxial cable.

4. An electrosurgical instrument according to claim 3, wherein the outer conductor of the coaxial cable is connected to the second electrode by a gas permeable conductive structure that is slidable relative to the second electrode or outer conductor of the coaxial cable and permits gas to flow through it.

5. An electrosurgical instrument according to claim 4, wherein the gas permeable conductive structure is any one of:
   a conductive mesh;
   a cage of radially extending conductive wires or springs; and
   a plurality of circumferentially spaced radially protruding dents.

6. An electrosurgical instrument according to claim 4, wherein the gas permeable conductive structure is soldered or crimped to the second electrode.

7. An electrosurgical instrument according to claim 2, wherein the second electrode is formed on a distal end of the sleeve, and the coaxial cable is retractable relative to the sleeve.

8. An electrosurgical instrument according to claim 7, wherein the second a conductive terminal tube mounted on the distal end of the sleeve, wherein the conductive terminal tube includes one or more radially projecting bumps on its inner surface for contacting the outer conductor of the coaxial cable.

9. An electrosurgical instrument according to claim 8, wherein the conductive terminal tube has an insulating liner around its inner surface, wherein the liner is located distally to the one or more radially projecting bumps.

10. An electrosurgical instrument according to claim 1, wherein the first electrode is a radiating microwave monopole antenna structure coupled to receive RF and/or microwave EM energy from the coaxial cable.

11. An electrosurgical instrument according to claim 10, wherein the radiating microwave monopole antenna structure comprises a cylinder of dielectric material having a hemispherical distal end surrounding, a length of the inner conductor of the coaxial cable which protrudes beyond the outer conductor and extends through the cylinder of dielectric material to protrude at its hemispherical distal end.

12. An electrosurgical instrument according to claim 11, wherein an end of the length of the inner conductor that protrudes from the hemispherical distal end of the cylinder is shaped into a hemisphere.

13. An electrosurgical instrument according to claim 1, wherein the probe is insertable through an instrument channel of an endoscope.

14. Electrosurgical apparatus for performing coagulation comprising:
a microwave signal generator for generating microwave EM energy;
an electrosurgical instrument according to claim 1 connected to receive the microwave EM energy;
a feed structure for conveying the microwave EM energy to the probe, the feed structure comprising a microwave channel for connecting the probe to the microwave signal generator,
a gas feed connected to supply gas to electrosurgical instrument,
wherein the apparatus is operable:
in a surface coagulation mode when the electrosurgical instrument is in the first configuration and gas, is supplied thereto, whereby the microwave EM energy delivered to the probe tip is arranged to strike and/or sustain a gas plasma between the first and second electrodes; and
in a deep tissue coagulation mode when the electrosurgical instrument is in the second configuration without gas supplied thereto, whereby the microwave EM energy delivered to the probe tip is arranged to emit a non-ionising electric field outwardly from the probe tip.

15. Electrosurgical apparatus according to claim 14 radiofrequency (RF) signal generator for generating RF electromagnetic (EM) energy having a first frequency, wherein:
the microwave EM energy has a second frequency that is higher than the first frequency,
the feed structure includes an RF channel for connecting the probe to the RF signal generator, and
in the surface coagulation mode, the apparatus is arranged to deliver the RF EM energy to the probe tip to strike the gas plasma between the first and second electrodes.

16. Electrosurgical apparatus according to claim 15 comprising a strike signal generation circuit arranged to cause a pulse of RF EM energy to be delivered to the probe to generate a high electric field across the flow path for striking the plasma, wherein the strike signal generation circuit includes control circuitry arranged to use a detectable characteristic of a pulse of microwave EM energy on the microwave channel to trigger generation of the pulse of RF EM energy.

17. Electrosurgical apparatus according to claim 14 comprising:
a microwave signal detector for sampling forward and reflected power on the microwave channel and generating therefrom a microwave detection signal indicative of microwave power delivered by the probe; and
a controller in communication with the microwave signal detector to receive the microwave detection signal,
wherein the controller, is operable to select an energy delivery profile for the microwave EM energy, the energy delivery profile for the microwave EM energy being for coagulation of tissue,
wherein the controller comprises a digital microprocessor programmed to output a microwave control signal for the microwave signal generator, the microwave control signal being for setting the energy delivery profile for the microwave EM energy, and
wherein the controller is arranged to determine a state for the microwave control signal based on the received microwave detection signal.

18. Electrosurgical apparatus according to claim 17 including a movement mechanism for causing relative movement between the first electrode and second electrode, wherein the controller is arranged to communicate a control signal to the movement mechanism based on the received microwave detection signal.

19. Electrosurgical apparatus according to claim 18, wherein the movement mechanism comprises any one of a linear motor, a stepper motor, a piezoelectric piezoelectric actuator, and a magnetostrictive actuator.

20. Electrosurgical apparatus according to claim 18, wherein the controller is arranged to adjustably control the movement mechanism to maintain a return loss from the probe at a value of at least 10 dB.

21. Electrosurgical apparatus according to claim 17, wherein, in the surface coagulation mode, the controller is arranged to cause the microwave signal generator to deliver a strike pulse of microwave EM energy to the probe to generate a high electric field across the flow path for striking the plasma.

22. Electrosurgical apparatus according to claim 21 including a quarter wave transformer that is switchable into the microwave channel to create the strike pulse of microwave EM energy.

23. Electrosurgical apparatus for performing coagulation comprising:
a radiofrequency (RF) signal generator for generating RF electromagnetic (EM) radiation having a first frequency;
a microwave signal generator for generating microwave EM radiation having a second is higher than the first frequency;
an electrosurgical instrument according to claim 1 connected to receive the RF EM radiation and the microwave EM radiation;
a feed structure for conveying the RF EM radiation and the microwave EM radiation to the probe, the feed structure comprising an RF channel for connecting the probe to the RF signal generator, and a microwave channel for connecting the probe to the microwave signal generator,
a gas feed connected to supply gas to electrosurgical instrument, wherein the apparatus is operable:
  in a surface coagulation mode when the electrosurgical instrument is in the first configuration and gas is supplied thereto, whereby the RF EM radiation delivered to the probe arranged to strike a gas plasma between the first and second electrodes; and
  in a deep tissue coagulation mode when the electrosurgical instrument is in the second configuration without gas supplied thereto, whereby the microwave EM radiation delivered to the probe tip is arranged to emit a non-ionising electric field outwardly from the probe tip.

* * * * *